United States Patent
Huang et al.

(10) Patent No.: US 9,795,650 B2
(45) Date of Patent: *Oct. 24, 2017

(54) ROMIDEPSIN FORMULATIONS AND USES THEREOF

(71) Applicant: Celgene Corporation, Summit, NJ (US)

(72) Inventors: Lianfeng Huang, Basking Ridge, NJ (US); Ho-Wah Hui, Basking Ridge, NJ (US); Vijay Naringrekar, Princeton, NJ (US); Gang Yang, Bridgewater, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/271,153

(22) Filed: Sep. 20, 2016

(65) Prior Publication Data

US 2017/0007665 A1    Jan. 12, 2017

Related U.S. Application Data

(63) Continuation of application No. 14/944,126, filed on Nov. 17, 2015, now Pat. No. 9,468,664, which is a continuation of application No. 14/581,999, filed on Dec. 23, 2014, now abandoned.

(60) Provisional application No. 61/921,361, filed on Dec. 27, 2013.

(51) Int. Cl.
| | |
|---|---|
| *A61K 38/15* | (2006.01) |
| *A61K 9/00* | (2006.01) |
| *A61K 47/10* | (2017.01) |
| *A61K 47/12* | (2006.01) |

(52) U.S. Cl.
CPC ............ *A61K 38/15* (2013.01); *A61K 9/0019* (2013.01); *A61K 47/10* (2013.01); *A61K 47/12* (2013.01)

(58) Field of Classification Search
CPC ............................... A61K 38/15; A61K 9/0019
See application file for complete search history.

(56) References Cited

U.S. PATENT DOCUMENTS

| | | |
|---|---|---|
| 4,977,138 A | 12/1990 | Okuhara et al. |
| 5,510,270 A | 4/1996 | Fodor et al. |
| 5,545,522 A | 8/1996 | Van Gelder et al. |
| 5,556,752 A | 9/1996 | Lockhart et al. |
| 5,578,832 A | 11/1996 | Trulson et al. |
| 5,605,793 A | 2/1997 | Stemmer |
| 5,716,785 A | 2/1998 | Van Gelder et al. |
| 5,776,905 A | 7/1998 | Gibbons et al. |
| 5,830,721 A | 11/1998 | Stemmer et al. |
| 5,837,458 A | 11/1998 | Minshull et al. |
| 5,891,636 A | 4/1999 | Van Gelder et al. |
| 6,117,679 A | 9/2000 | Stemmer |
| 6,391,640 B1 | 5/2002 | Minshull et al. |
| 6,403,555 B1 | 6/2002 | Skov et al. |
| 6,548,479 B1 | 4/2003 | Skov et al. |
| 6,706,686 B2 | 3/2004 | Long et al. |
| 6,777,217 B1 | 8/2004 | Schreiber et al. |
| 6,809,118 B2 | 10/2004 | Chung et al. |
| 6,828,302 B1 | 12/2004 | Skov et al. |
| 6,905,669 B2 | 6/2005 | DiMartino |
| 6,946,441 B2 | 9/2005 | Long et al. |
| 7,041,639 B2 | 5/2006 | Skov et al. |
| 7,056,883 B2 | 6/2006 | Ito et al. |
| 7,056,884 B2 | 6/2006 | Nakajima et al. |
| 7,148,204 B2 | 12/2006 | Bennett et al. |
| 7,171,311 B2 | 1/2007 | Dai et al. |
| 7,314,862 B2 | 1/2008 | Naoe et al. |
| 7,354,928 B2 | 4/2008 | Wang et al. |
| 7,396,665 B2 | 7/2008 | Ueda et al. |
| 7,470,722 B2 | 12/2008 | Malecha et al. |
| 7,488,712 B2 | 2/2009 | Yoshida et al. |
| 7,857,804 B2 | 12/2010 | McCaffrey et al. |
| 2003/0162293 A1 | 8/2003 | Chu et al. |
| 2004/0018968 A1 | 1/2004 | Sgouros et al. |
| 2004/0053820 A1 | 3/2004 | Nakajima et al. |
| 2004/0072735 A1 | 4/2004 | Richon et al. |
| 2004/0077591 A1 | 4/2004 | Dangond |
| 2004/0127523 A1 | 7/2004 | Bacopoupos et al. |
| 2004/0228909 A1 | 11/2004 | Sarris et al. |
| 2005/0059682 A1 | 3/2005 | Rubinfeld |
| 2005/0070467 A1 | 3/2005 | Naoe et al. |

(Continued)

FOREIGN PATENT DOCUMENTS

| | | |
|---|---|---|
| CA | 2317003 | 8/2001 |
| EP | 0352646 | 1/1990 |

(Continued)

OTHER PUBLICATIONS

Piekarz et al, Phase 2 trial of romidepsin in patients with peripheral T-cell lymphoma, Blood, Jun. 2, 2011, vol. 117, No. 22, pp. 5827-5824.*
Whitehead et al., Phase II Trial of Depsipeptide (NSC-630176) in Previously Treated Colorectal Cancer Patients with Advanced Disease: A Southwest Oncology Group Study (S0336). Invest New Drugs. Oct. 2009 ; 27(5): 469-475.*
Delloyd's Lab Tech, Preparation of pH buffer solutions, 5 pages, from http://delloyd.50megs.com/moreinfo/buffers2.html, 2000 (Delloyd).*
Gennaro ("Remington's Pharmaceutical Sciences"; 1990; 18th Ed., Mack Publishing Co. Easton, PA, pp. 218-219, 241-242,1549-1550 (Gennaro).*
Williams and Amidon, Excess Free Energy Approach to the Estimation of Solubility in Mixed Solvent System III: Ethanol-Propylene Glycol-Water Mixtures, J. of Pharm. Sci, vol. 73, No. 1, Jan. 1984.*

(Continued)

*Primary Examiner* — Karlheinz R Skowronek
*Assistant Examiner* — Joseph Fischer
(74) *Attorney, Agent, or Firm* — Jones Day

(57) ABSTRACT

Provided herein are liquid concentrate formulations of romidepsin. Also provided are methods for producing these formulations and uses thereof. In one embodiment, the formulation comprises romidepsin, polyethylene glycol, etanol and a citrate buffer. In another embodiment, the formulation comprises romidepsin, polyethylene glycol, etanol and an acetate buffer.

12 Claims, No Drawings

(56) References Cited

U.S. PATENT DOCUMENTS

| | | |
|---|---|---|
| 2005/0187148 A1 | 8/2005 | Naoe et al. |
| 2005/0187149 A1 | 8/2005 | Naoe et al. |
| 2005/0191713 A1 | 9/2005 | Sasakawa et al. |
| 2005/0222013 A1 | 10/2005 | Jung et al. |
| 2005/0272647 A1 | 12/2005 | Yamaji et al. |
| 2006/0018921 A1 | 1/2006 | Levenson et al. |
| 2006/0019883 A1 | 1/2006 | Kronblad et al. |
| 2006/0100140 A1 | 5/2006 | Dent et al. |
| 2006/0106049 A1 | 5/2006 | Odenike |
| 2006/0128660 A1 | 6/2006 | Rajski et al. |
| 2006/0135413 A1 | 6/2006 | Naoe et al. |
| 2006/0223747 A1 | 10/2006 | Ito et al. |
| 2006/0270016 A1 | 11/2006 | Holm |
| 2007/0015787 A1 | 1/2007 | Bruncko et al. |
| 2007/0110719 A1 | 5/2007 | Holm |
| 2007/0129290 A1 | 6/2007 | Or et al. |
| 2007/0148228 A1 | 6/2007 | Cumming et al. |
| 2007/0292512 A1 | 12/2007 | Leonard et al. |
| 2008/0214446 A1 | 9/2008 | Okada et al. |
| 2008/0233562 A1 | 9/2008 | Sasakawa et al. |
| 2009/0186382 A1 | 7/2009 | Verdine et al. |
| 2009/0209616 A1 | 8/2009 | Verdine et al. |
| 2009/0221473 A1 | 9/2009 | Chan et al. |
| 2010/0093610 A1* | 4/2010 | Vrolijk .................. A61K 38/15 514/1.1 |

FOREIGN PATENT DOCUMENTS

| | | |
|---|---|---|
| EP | 1010705 | 6/2000 |
| EP | 1426054 | 6/2004 |
| JP | H0764872 | 7/1995 |
| JP | 11-335375 | 12/1999 |
| JP | 2001-348340 | 12/2001 |
| WO | WO 98/39965 | 9/1998 |
| WO | WO 98/40080 | 9/1998 |
| WO | WO 01/18171 | 3/2001 |
| WO | WO 01/42282 | 6/2001 |
| WO | WO 02/06307 | 1/2002 |
| WO | WO 02/15921 | 2/2002 |
| WO | WO 02/20817 | 3/2002 |
| WO | WO 02/86498 | 4/2002 |
| WO | WO 02/97053 | 5/2002 |
| WO | WO 02/055017 | 7/2002 |
| WO | WO 02/055688 | 7/2002 |
| WO | WO 02/085400 | 10/2002 |
| WO | WO 02/090534 | 11/2002 |
| WO | WO 03/015810 | 2/2003 |
| WO | WO 03/017763 | 3/2003 |
| WO | WO 03/024442 | 3/2003 |
| WO | WO 03/035843 | 5/2003 |
| WO | WO 03/053468 | 7/2003 |
| WO | WO 03/070188 | 8/2003 |
| WO | WO 03/083067 | 10/2003 |
| WO | WO 03/084611 | 10/2003 |
| WO | WO 03/088954 | 10/2003 |
| WO | WO 03/103613 | 12/2003 |
| WO | WO 2004/009771 | 1/2004 |
| WO | WO 2004/017996 | 3/2004 |
| WO | WO 2004/024160 | 3/2004 |
| WO | WO 2004/062654 | 7/2004 |
| WO | WO 2004/064727 | 8/2004 |
| WO | WO 2004/074478 | 9/2004 |
| WO | WO 2004/096289 | 11/2004 |
| WO | WO 2004/098495 | 11/2004 |
| WO | WO 2005/000282 | 1/2005 |
| WO | WO 2005/000289 | 1/2005 |
| WO | WO 2005/000332 | 1/2005 |
| WO | WO 2005/009961 | 2/2005 |
| WO | WO 2005/018578 | 3/2005 |
| WO | WO 2005/023179 | 3/2005 |
| WO | WO 2005/027842 | 3/2005 |
| WO | WO 2005/030239 | 4/2005 |
| WO | WO 2005/051430 | 6/2005 |
| WO | WO 2005/052143 | 6/2005 |
| WO | WO 2005/053609 | 6/2005 |
| WO | WO 2005/058298 | 6/2005 |
| WO | WO 2005/079827 | 9/2005 |
| WO | WO 2005/085864 | 9/2005 |
| WO | WO 2005/087206 | 9/2005 |
| WO | WO 2005/105055 | 11/2005 |
| WO | WO 2005/105066 | 11/2005 |
| WO | WO 2005/115149 | 12/2005 |
| WO | WO 2005/117930 | 12/2005 |
| WO | WO 2006/027346 | 3/2006 |
| WO | WO 2006/055621 | 5/2006 |
| WO | WO 2006/060382 | 6/2006 |
| WO | WO 2006/060429 | 6/2006 |
| WO | WO 2006/129105 | 12/2006 |
| WO | WO 2007/009539 | 1/2007 |
| WO | WO 2007/040522 | 4/2007 |
| WO | WO 2007040522 | 4/2007 |
| WO | WO 2007/058896 | 5/2007 |
| WO | WO 2007/061939 | 5/2007 |
| WO | WO 2007/145704 | 12/2007 |
| WO | WO 2007/146730 | 12/2007 |
| WO | WO 2008/013589 | 1/2008 |
| WO | WO 2008/083290 | 7/2008 |
| WO | WO 2012/037008 | 3/2012 |
| WO | WO 2013/106696 | * 7/2013 ............ A61K 38/15 |

OTHER PUBLICATIONS

Iwamoto et al., A phase I/II trial of the histone deacetylase inhibitor romidepsin for adults with recurrent malignant glioma: North American Brain Tumor Consortium Study 03-03, Neuro-Oncology 13(5):509-516, 2011.*

Niesvizky et al., Phase II trial of the histone deacetylase inhibitor romidepsin for the treatment of refractory multiple myeloma, Cancer. Jan. 15, 2011; 117(2): 336-342.*

Cancer Drug Design and Discovery Neidle, Stephen, ed. (Elsevier/Academic Press, 2008) p. 431.*

Abolghasem Jouyban, Review of the cosolvency models for predicting solubility of drugs in water-cosolvent mixtures, J. Pharm Pharmaceut Sci 11(1):32-58 (2008).*

Strickley et al., Solubilizing Excipients in Oral and Injectable Formulations, 2004, Pharmaceutical Research, 21(2):201-230.*

R. Spector, The War on Cancer A Progress Report for Skeptics, Skeptical Inquirer, vol. 34.1, Jan./Feb. 2010, 11 pages.*

Istodax Prescribing Information document, 2011, 9 pages, Celgene Corp.*

Aron et al., "Depsipeptide (FR901228) induces histone acetylation and inhibition of histone deacetylase in chronic lymphocytic leukemia cells concurrent with activation of caspase 8-mediated apoptosis and down-regulation of c-FLIP protein," Blood, 102(2):652-658 (2003).

Bates et al., "Final Clinical Results of a Phase 2 NCI Multicenter Study of romidepsin in Recurrent Cutaneous T-Cell Lymphoma (Molecular Analyses Included)," ASH Annual Meeting Abstracts, 112(11): p. 1568 (2008).

Berge et al., "Pharmaceutical Salts," J Pharm Science 66:1-19, 1977.

Bhalla, "Epigenetic and chromatin modicifers as targeted therapy of hematologic malignancies," J Clin Oncol, 23(17):3971-3993 (2005).

Bishton et al., "Epigenetic target in hematological malignancies: combination therapies with HDAC's and demethylating agents," Expert Rev Anticancer Ther, 7(10):1439-1449 (2007).

Bogden et al., "Growth of Human Tumor Xenografts Implanted under the Renal Capsule of Normal Immunocompetent Mice," Exp Cell Biol 47:281-293 (1979).

Bolden et al., "Anticancer activities of histone deacetylase inhibitors," Nat Rev Drug Discovery, 5(9):769-784 (2006).

Budillon et al., "Growth arrest, apoptosis and potentiation of 5-fluorouracil and Raltitrexed cytotoxic effect induced by histone deacetylase inhibitor Saha in colorectal cancer cells," Eur J Cancer 38:S29 (2002).

Butler et al., "Suberoylanilide Hydroxamic Acid, an Inhibitor of Histone Deacetylase, Suppresses the Growth of Prostate Cancer Cells in Vitro and in Vivo," Cancer Res 60:5165-5170 (2000).

(56) References Cited

OTHER PUBLICATIONS

Byrd et al., "A phase 1 and pharmacodynamic study of depsipeptide (FK228) in chronic lymphocytic leukemia and acute myeloid leukemia," Blood, 105(3):959-967 (2005).
Byrd et al., "Depsipeptide (FR901228): a novel therapeutic agent with Selective in vitro activity against human B-cell chronic lymphocytic leukemia cells ," Blood, 94(4):1401-1408 (1999).
Catley et al., "Aggresome induction by proteasome inhibitor bortezpmib and {alpha}-tubulin hyperacetylation by tubulin deacetylase (TDAC) inhibitor LBH589 are synergistic in myeloma cells," Blood 108(10):3441-3449 (2006).
Chan et al., "Depsipeptide (FR901228, NSC-630176) pharmacokinetics in the rat by LC/MS/MS," Invest New Drugs,15(3):195-206 (1997).
Cheson et al., "New Drugs for the Treatment of Chronic Lymphocytic Leukemia," Reviews Clin Exp Hematol 4(2):145-166 (2000).
Conway et al., "Vincristine-and Cisplatin-induced Apoptosis in Human Retinoblastoma. Potentiation by Sodium Butyrate," Eur J Cancer, 34(11):1741-1748 (1998).
Dai et al., "Interactions between bortezomib and romidepsin and belinostat in chronic lymphocytic leukemia cells," Clin Cancer Res, 14(2):549-558 ( 2008).
Database Biosis 'Online, AN-PREV200400024248, XP-002342749, "Anti-Tumor Efficacy of Four Different Histone Deacetylase Inhibitors on Hepatoma Cells in Vitro", 2003 (Abstract No. T1786).
Dokmanovic & Marks, "Prospects: histone deacetylase inhibitors," J Cell Biochem, 96(2):293-304 (2005).
Fiebig et al., "Bcl-XL is qualitatively different from and ten times more effective than Bcl-2 when expressed in a breast cancer cell line," Cancer, 6:213 (2006).
Findley et al., "Expression and Regulation of Bcl-2, Bcl-xl, and Bax Correlate With p53 Status and Sensitivity to Apoptosis in Childhood Acute Lymphoblastic Leukemia," Blood, 89(8): 2986-2993 (1997).
Finnin et al., "Structures of a histone deacetylase homologue bound to the TSA and SAHA Inhibitors," Nature, 401(6749):188-193 (1999).
Fischer et al., $41^{st}$ Annual Meeting of the American Society of Clinical Oncology, Abstr # 3106 (2005).
Fukumura et al., "A sensitive transcriptome analysis method that can detect unknown transcripts," Nucl Acids Res 31(16):e94 (2003).
Furumai et al.," FK228 (depsipeptide) as a natural prodrug that inhibits class I histone deacetylases," Cancer Res, 62(17):4916-4921 (2002).
Garcia-Manero et al., "Phase 1/2 study of the combination of 5-aza-2'-deoxycytidine with valporic acid in patients with leukemia," Blood, 108(10):3271-3279 (2006).
Geldof et al., "Cytotoxicity and neurocytoxicity of new marine anticancer agents evaluacted using in vitro assays," Cancer Chemother & Pharmacol 44(4):312-318 (1999).
Gore et al., "Combined DNA methyltransferase and histone deacetylase inhibition in the treatment of myeloid neoplasms," Cancer Res, 66(12):6361-6369 (2006).
Gore et al., "Impact of the putative differentiating agent sodium phenylbutyrate on myelodysplastic syndromes and acute myeloid leukemia," Clin Cancer Res, 7(8):2330-2339 (2001).
Han et al., "Apicidin, a Histone Deacetylase Inhibitor Inhibits Proliferation of Tumor Cells via Induction of p21 WAF1/Cip1 and Gelsolin," Cancer Res 60(21):6068-6074 (2000).
Harrison et al., "High Response Rates with the Combination of Bortezomib, Dexamethasone and the Pan-Histone Deacetylase Inhibitor Romidepsin in Patients with Relapsed or Refractory Multiple Myeloma in Phase I/II Clinical Trial," ASH Annual Meeting Abstracts, 112(11):3698 (2008).
Inoue et al., "Subrenal capsule assay-an experimental study and clinical application to chemosensitivity tests," Gan to Kagaku Ryoho 14(5Pt2):1629-1635 (1987) (Abstract).
Jones & Baylin, "The Epigenomics of Cancer," Cell 128:683-692 (2007).

Jones & Baylin, "The fundamental role of epigenetic events in Cancer," Nat Rev Genet, 3(6):415-428 (2002).
Jung et al., "Amide Analogues of Trichostatin A as Inhibitors of Histone Deacetylase and Inducers of Terminal Cell Differentiation," J Med Chem US 42(22):4669-4679 (1999).
Khan et al., "Total Synthesis of the Antitumor Depsipeptide FR-901,228," J Am Chem Soc 118:7237-7238, (1996).
Kano et al., "The Joint Meeting of the $64^{th}$ Annual Meeting of the Japanese Society of Hematology and the $44^{th}$ Annual Meeting of the Japanese Society of Clinical Hematology," Japanese J Clin Hematology 43(8):116 (2002).
Kawamoto et al., "Expression Profiling by iAFLP: A PCR-Based Method for Genome-Wide Gene Expression Profiling," Genome Res 12:1305-1312 (1999).
Khan et al., "Analysis of histone deacetylase inhibitor, depsipeptide (FR901228), effect on multiple myeloma," Br J Haematol, 125(2):156-161 (2004).
Kim et al., "Clinically significant responses Achieved with Romidepsin in Treatment-Refractory Cutaneous T-Cell Lymphoma: Final Results from a Phase 2B, International, Multicenter, Registration Study," ASH Annual Meeting Abstracts, 112(11):263 (2008).
Kisselev & Goldberg, "Proteasome inhibitors: from research tools to drug candidates," Chem Biol 8:739-758 (2001).
Kitazono et al., "Enhanced Adenovirus Transgene Expression in Malignant Cells Treated with the Histone Deacetylase Inhibitor FR901228," Cancer Res 61:6328-6330 (2001).
Kitazono et al., "Adenovirus HSV-TK Constuct with Thyroid-Specific Promoter: Enhancement of Activity and Specificity with Histone Deacetylase Inhibitors and Agents Modulating the Camp Pathway," Int J Cancer 99:453-459 (2002).
Kitazono et al., "Low Concentrations of the Histone Deacetylase Inhibitor, Depsipeptide (FR901228), Increase Expression of the Na/I Symporter and Iodine Accumulation in Poorly Differentiated Thyroid Carcinoma Cells," J Clin Endocrin 86(7):3430-3435 (2001).
Kitazono et al., Proc Amer Assoc Cancer Res Annual 43:799 (2002) (Abstract only).
Klimek et al., "Tolerability, pharmacodynamics, and pharmacokinetics studies fo depsipeptide (romidepsin) in patients with acute myelogenous leukemia or advanced myelodysplastic syndromes," Clin Cancer Res, 14(3):826-832 (2008).
Klisovic et al., "Depsipeptide (FR9801228) Inhibits Proliferation and Induces Apoptosis in Primary and metastatic Human Uveal Melanoma Cell Lines," Invest Ophthalmol Vis Sci, 44(6):2390-2398 (2003).
Komatsu et al., "Cyclic Cyfroxamic-acid-containing Peptide 31, a Potent Syntheic Histone Deacetylase Inhibitor with Antitumor Activity," Cancer Res 61(11):4459-4466 (2001).
Kosugi et al., "In vivo Effects of a Histone Deacetylase Inhibitor, FK228, on Human Acute Promyelocytic Leukemia in NOD/Shi-scid/scid Mice," Japanese J Cancer Res 92(5):529-536 (2001).
Kuendgen et al., "Treatment of myelodysplastic syndromes with valproic acid alone or in combination with all-trans retinoic acid," Blood, 104(5):1266-1269 (2004).
Liakopoulou et al., "Stimulation of Fetal Hemoglobin Production by Short Chain Fatty Acids," Blood, 86:3227 (1995).
Maeda et al., "Up-regulation of costimulatory/adhesion molecules by histone deacetylase ihibitors in acute myeloid leukemia cells," Blood, 96(12):3847-3856 (2000).
Magner et al., "Activation of MHC class I, II, and CD40 gene expression by histone deacetylose inhibitors," J Immunol, 165(12):7017-7024 (2000).
Marks et al., "Histone deacetylase inhibitors: Inducers of differentiation or apoptosis of transformed cells," J Natl Cancer Inst, 92(15):1210-1216 (2000).
Marshall et al., "A phase I trial of depsipeptide (FR901228) in patients with advanced cancer," J Exp Ther Oncol, 2(6):325-332 (2002).
Mertins et al., Proc Amer Assoc Cancer Res Annual Meetins 40:623 (1999).
Mitsiades et al., "Transcriptional signature of histone deacetylase inhibition in multiple myeloma: biological and clinical implications," Proc Natl Acad Sci USA, 101(2):540-545 (2004).

(56) References Cited

OTHER PUBLICATIONS

Molife et al.,"Phase II study of FK228 in patients with hormone refractory prostate cancer (HRPC)," J Clin Oncol (Meeting Abstracts), 24(18 Suppl):14554 (2006).

Murata et al., "Apoptotic Cytotoxic Effects of a Histone Deacetylase Inhibitor, FK228, on Malignant Lymphoid Cells," Japanese J Cancer Res 91:1154-1160 (2000).

Nakajima et al., ", FR901228, a potent antitumor antibiotic, is a novel histone det1cetylose inhibitor," Exp Cell Res, 241(1)126-133 (1998).

Nebbioso et al., "Tumor-selective action of HDAC inhibitors involves TRAIL induction in acute myeloid leukemia cells," Nat Med, 11(1):77-84 (2005).

Nebozhyn et al., "Quantitative PCR on 5 genes reliably Identifies CTCL patients with 5% to 99% circulating tumor cells with 90% accuracy," Blood, 107(8):3189-3196 (2006).

Newbold et al., "Characterisation of the novel apoptotic and therapeutic activities of the histone deacetylase inhibitor romidepsin," Mol Cancer Ther, 7(5):1066-1079 (2008).

Niesvizky et al., "Multicenter Phase II Trial of the Histone Deacetylase Inhibitor Depsipeptide (FK228) for the Treatment of Relapsed or Refractory Multiple Myeloma (MM)," Blood ASH Annual Meeting Abstracts, 106(11):2574 (2005).

Nishimura et al., "A New Antitumor Antibiotic, FE900840," J Antibiot XLII(4):553-557 (1989).

Nuijen et al., "Development of a lyophilized parenteral pharmaceutical formulation the investicational polypeptide marine anticancer agent kahalalide F.," Medline (2001) XP-002206588.

Odenike et al., "Histone deacetylase inhibitor romidepsin has differential activity in core binding factor acute myeloid leukemia," Cancer Res, 14(21):7095-7101 (2008).

Paoluzzi et al., "Romidepsin and belinostat synergize the antineoplastic effect of bortezomib in mantle cell lymphoma," Clin Cancer Res, 16(2):554-565 (2010).

Peart et al., "Novel mechanisms of apoptosis induced by histone deacetylase inhibitors," Cancer Res, 63(15):4460-4471 (2003).

Peart et al., "Identification and functional significance of genes regulated by structurally different histone deacetylose inhibitors," Proc Natl Acad Sci USA, 102(10):3697-3702 (2005).

Pei et al., "Synergistic induction of oxidative injury and apoptosis in human multiple myeloma cells by the proteasome inhibitor bortezpmib and histone deacetylase inhibitors," Clin Cancer Res, 10(11):3839-3852 (2004).

Piekarz et al., "Completion of the First Cohort of Patients with Cutaneous T-Cell Lymphoma Enrolled on a Phase II Trial of Depsipeptide," ASH Annual Meeting Abstracts,106(11):231 (2005).

Piekarz et al., "Results of a Phase 2 NCI Multicenter Study of Romidepsin in Patients with Relapsed Peripheral T-Cell Lymphoma (PTCL)," ASH Annual Meeting Abstracts 112(11):1567 (2008).

Piekarz et al., "T-cell lymphoma as a model for the use of histone deacetylase inhibitors in cancer therapy: impact of depsipeptide on molecular markers, therapeutic targes, and mechanisms of resistance," Blood , 103(12):4636-4643 (2004).

Piekarz et al., "Inhibitor of histone deactylation, depsipeptide (FR901228), in the treatment of peripheral and cutaneous T-cell lymphoma: a case report," Blood , 98(9):2865-2868 (2001).

Piekarz et al., "Cardiac studies in patients treated with depsipeptide, FK228,1n a phase II trial for T-cell lymphoma," Clin Cancer Res, 12(12):3762-3773 (2006).

Piekarz et al., "Epigenetic modifiers: basic understanding and clinical development," Clin Cancer Res, 15(12):3918-3926 (2009).

Piekarz et al., "Phase II Multi-Institutional Trial of the Histone Deacetylase Inhibitor Romidepsin As Monotherapy for Patients With Cutaneous T-Cell Lymphoma," J Clin Oncol, 27(32):5410-5417 (2009).

Piekarz et al., "A Review of Depsipeptide and Other Histone Deacetylase Inhibitors in Clinical Trials," Curr Pharm Des 10:2289-2298 (2004).

Piekarz, R., et al, "Update of the NCI multiinstutional phase II trial of romidepsin, FK228,for patients with cutaneous or peripheral T-cell lymphoma,". J Clio Oncol (Meeting Abstracts), 2007.25(18__ suppl): p. 8027 (2007).

Prince et al., "Clinical studies of histone deacetylase inhibitors," Clin Cancer Res, 15(12):3958-3969 (2009).

Program of the 4th Japanese Foundation for Cancer Research, International Symposium on Cancer Therapy (ISCC), Feb. 12, 1999.

Rasheed et al., "Histone deacetylase inhibitors in cancer therapy," Expert Opin Investig Drugs, 16(5):659-678 (2007).

Richon et al., "Histone Deacetylase Inhibitors: A New Class of Potential Therapeutic Agents for Cancer Treatment," Clin Cancer Res 8(3):662-664 (2002).

Richon et al., "Histone deacetylasei inhibitor selectively induces p21WAFI expression and gene-associated histone acetylation," Proc Natl Acad Sci USA, 97(18):10014-10019 (2000).

Robey et al., "Increased MDRI expression in normal and malignant peripheral blood mononuclear cells obtained from patients receiving depsipetide• (FR901228, FK228, NSC630176)," Clin Cancer Res, 12(5):1547-1555 (2006).

Roychowdhury et al., "Selective efficacy of depsipeptide in a xenograft model of Epstein-Barr virus-positive lymphoproliferative disorder ," J Natl Cancer Inst, 96(19):1447-1457 (2004).

Sakai et al., "MBD3 and HDACI,two components of the NuRDcomplex, are localized at Aurora-A-positive centrosomes in M phase," J Biol Chem, 277(50):48714-48723 (2002).

Sandor et al., "P21-dependent G arrent with downregulation of cyclin D1 upregulation of cyclin E by the histone deacetylase inhibitor FR901228," Br J Cancer 83(6):817-825, (2000).

Sandor et al., "Phase I trial of the histone deacetylase Inhibitor, depsipeptide (FR901228, NSC 630176), In patients with refractory neoplasms," Clin Cancer Res, 8(3):718-728 (2002).

Sasakawa et al., "Effects of FK228, a novel histone deacetylase inhibitor, on human lymphoma U-937 cells in vitro and in vivo," Biochem Pharmacol, 64(7):1079-1090 (2002).

Sawa et al., "Histone deacetylase Inhibitor, FK228, Induces apoptosis and suppresses cell roliferation of human glioblastoma cells in vitro and in vivo," Acta Neuropathol (Berlin), 07(6):523-531 (2004).

Sawa et al., "Anti-tumor effects of Hitone deacetylase inhibitors against human glioma cells," Proc of Japanese Cancer Assoc 60:597 (2001) (w/English translation).

Schrump et al., "Clinical and molecular responses in lung cancer patients receiving romidepsin," Clin Cancer Res, 14(1):188-198 (2008).

Schwartsmann et al., "Marine organisms as a source of new anticancer agents," The Lancet Oncology 2(4):221-225 (2001).

Sreedharan et al., "Relevance of circadian closing time for the tolerability of germcitabine as a single agent of combined with cisplatin in mice," Proc Amer Assoc Cancer Res 44(2 ed.):742 (2003) (XP-001154773).

Stadler et al., "A phase II study of depsipeptide in refractory metastatic renal cell cancer" Clin Genitourin Cancer, 5(1):57-60 (2006).

Su et al., "A phase II study of single agent depsipeptide (DEP) in patients (pts) with radioactive iodine (RAI)-refractory, metastatic,thyroid carcinoma: Preliminary toxicity and efficacy experience," J Clin Oncol (Meeting Abstracts), 24(18 Suppl):5554 (2006).

Sutheesophon et al., "Histone deacetylase inhibitor depsipeptide (FK228) induces apoptosis in leukemic cells by facilitating mitochondrial translocation of Bax, which is enhanced by the proteasome Inhibitor bonezpmib," Acta Haematol, 115(1-2):78-90 (2006).

Ueda et al., "Action of FR901228, a novel antitumor bicyclic depsipeptide produced by Chromobacterium violaceum No. 968, on Ha-ras transformed NIH3T3 cells," Biosci Biotechnol Biochem, 58(9):1579-1583 (1994).

Ueda et al., "FR901228, a novel antitumor bicyclic depsipeptide produced by Chromobacterium violaceum No. 968. I. Taxonomy, fermentation, isolation, physico-chemical and biological properties, and antitumor activity," J Antibiot (Tokyo),47:301-310, (1994).

(56) References Cited

OTHER PUBLICATIONS

Ueda et al., "FR901228, A Novel Antitumor Bicyclic Depsipeptide Produced by Chromobacterium violaceum No. 968," J Antibiot (Tokyo) 47:315-323 (1994).

Ueda et al., "Expression of a full-length cDNA for the human "MDR1" gene confers resistance to colchicines, doxorubicin, and vinblastine," PNAS USA 84:3004 (1987).

Vrana et al., "Induction of apoptosis in U937 human leukemia cells by suberoylanilide hydroxamic acid (SAHA) proceeds through pathways that are regulated by Bcl-2/Bcl-XL, c-Jun, and p21CIPI, but independent of p53," Oncogene, 18(50):7016-7025 (1999).

Wang et al., "Fungal metabolite FR901228 inhibits c-Myc Fas ligand expression," Oncogene 17:1503-1508 (1998).

Watanabe et al., "Induction of autophagy in malignant rhabdoid tumor cells by the histone deacetylase inhibitor FK228 through AIF translocation," Int J Cancer,124(1):55-67 (2009).

Weidle et al. "Inhibition of Histone Deacetylases: a New Strategy to Target Epigentic Modifications for Anticancer Treatment," Anticancer Res 20:1471-1486 (2000).

Whitehead et al., "Phase II trial of depsipeptide (NSC-630176) in colorectal cancer patients who have received either one or two prior chemotherapy regimens for nwrARrux or locally advanced, unresectable disease: A Southwest Oncology Group study," J Clin Oncol (Meeting Abstracts), 24(18 Suppl):3598 (2006).

Whittaker et al., "international multicenter phaSe II study of the HDAC inhibitor (HDAC) depsipeptide (FK228) in cutaneous T-cell lymphoma (CTCL): Interim report," J Clin Oncol (Meeting Abstracts), 24(18 Suppl):3063 (2006).

Xiao et al., "Identification of thiols and glutathione conjugates of depsipeptide FK228 (FR901228), a novel hostone protein deacetylase inhibitor, in the blood," Rapid Commun Mass Spectrom 17:757-766 (2003).

Xiao et al., "Efflux of Depsipeptide FK228(FR901228, NSC-630176) Is Mediated by P-Glycoprotein and Multidrug Resistance-Associate Protein 1," J Pharm & Exp Therapeutics 313(1):268-276 (2005).

Yu et al., "The proteasome inhibitor bortezpmib interacts synergistically with histone deacetylase inhibitors to induce apoptosis in Bcr/Abl+ cells sensitive and resistant to STI571," Blood, 102(10):3765-3774 (2003).

Non final office action for U.S. Appl. No. 13/740,063 dated Apr. 21, 2014.

Non final office action for U.S. Appl. No. 13/740,063 dated May 22, 2013.

Final office action for U.S. Appl. No. 13/740,063 dated Nov. 4, 2013.

Non final office action for U.S. Appl. No. 14/944,126 dated Dec. 16, 2015.

Notice of allowance for U.S. Appl. No. 14/944,126 dated Jun. 21, 2016.

* cited by examiner

ROMIDEPSIN FORMULATIONS AND USES THEREOF

CROSS REFERENCE TO RELATED APPLICATIONS

This application is a continuation application of U.S. Ser. No. 14/944,126, filed Nov. 17, 2015, now allowed, which is a continuation application of U.S. Ser. No. 14/581,999 filed Dec. 23, 2014, now abandoned, which claims the benefit of priority to U.S. Provisional application Ser. No. 61/921,361 filed Dec. 27, 2013, the disclosures of which are incorporated by reference herein in their entireties.

FIELD

Provided herein are liquid formulations of romidepsin. Also provided are methods for producing these formulations and uses thereof.

BACKGROUND

Cancer is a major public health problem in the United States and in the world. Currently, one in 4 deaths in the United States is due to cancer. Each year, the American Cancer Society estimates the numbers of new cancer cases and deaths expected in the United States in the current year and compiles the most recent data on cancer incidence, mortality, and survival based on incidence data from the National Cancer Institute, the Centers for Disease Control and Prevention, and the North American Association of Central Cancer Registries and mortality data from the National Center for Health Statistics. A total of 1,596,670 new cancer cases and 571,950 deaths from cancer were projected to occur in the United States in 2011. Overall cancer incidence rates were stable since late 1990s. The reduction in the overall cancer death rates since 1990 in men and 1991 in women translated to the avoidance of about 898,000 deaths from cancer. Despite an obvious progress, approximately 560,000 people died of cancer in 2006 in the United States alone. Aging of the general population and development of new forms of cancer contribute to the problem.

Romidepsin has been shown to have anticancer activities. The drug is approved in the U.S. for treatment of cutaneous T-cell lymphoma (CTCL) and peripheral T-cell lymphoma (PTCL), and is currently being tested, for example, for use in treating patients with other hematological malignancies (e.g, multiple myeloma, etc.) and solid tumors (e.g., prostate cancer, pancreatic cancer, etc.). It is thought to act by selectively inhibiting deacetylases (e.g., histone deacetylase, tubulin deacetylase), promising new targets for development of a new class of anti-cancer therapies (Bertino & Otterson, *Expert Opin Investig Drugs* 20(8):11151-1158, 2011). One mode of action involves the inhibition of one or more classes of histone deacetylases (HDAC).

As cancer remains a major worldwide public health problem, there is a continued need for effective therapies to treat cancer.

SUMMARY

In one embodiment, provided herein is a romidepsin formulation. In one embodiment, the formulation is a liquid concentrate formulation. In one embodiment, the formulation is a liquid concentrate formulation for dilution. In one embodiment, a liquid concentrate formulation for dilution is formulated in a solvent system. In one embodiment, the solvent system comprises a citrate buffer. In another embodiment, the solvent system comprises an acetate buffer. In one embodiment, a romidepsin formulation is an injectable formulation.

In one embodiment, provided herein are methods to treat proliferative diseases using a romidepsin formulation provided herein. In some embodiments, provided herein are methods to treat cancer. In some embodiments, cancers include, but are not limited to, carcinomas, sarcomas, leukemias, lymphomas and the like. In certain embodiments, the cancer is a hematological malignancy. In certain embodiments, the cancer is a solid tumor.

In one embodiment, provided are methods of producing a romidepsin formulation.

DETAILED DESCRIPTION

Definitions

As used in the specification and the accompanying claims, the indefinite articles "a" and "an" and the definite article "the" include plural as well as singular referents, unless the context clearly dictates otherwise.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound or dosage form provided herein, with or without one or more additional active agent(s), after the diagnosis or the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, and unless otherwise specified, "amelioration" of the symptoms of a particular disorder by administration of a particular pharmaceutical composition refers to any lessening, whether permanent or temporary, lasting or transient, that can be attributed to or associated with the administration of the composition.

As used herein, and unless otherwise specified, the term "therapeutically effective amount" or "effective amount" of a compound means an amount sufficient to provide a therapeutic benefit in the treatment or management of a disease or disorder, or to delay or minimize one or more symptoms associated with the disease or disorder. A "therapeutically effective amount" or "effective amount" of a compound means an amount of therapeutic agent, alone or in combination with one or more other agent(s), which provides a therapeutic benefit in the treatment or management of the disease or disorder. The terms "therapeutically effective amount" and "effective amount" can encompass an amount that improves overall therapy, reduces, delays, or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice, and the like. In specific embodiments, the subject is a human. The terms "subject" and "patient" are used interchangeably herein in reference, for example, to a mammalian subject, such as a human. In particular embodiments, a subject having cancer is a subject who has been previously diagnosed as having cancer.

As used herein, and unless otherwise specified, "neoplasm" is an abnormal mass of tissue as a result of neoplasia. The growth of neoplastic cells exceeds and is not coordinated with that of the normal tissues around it. The growth persists in the same excessive manner even after cessation of the stimuli. It usually causes a lump or tumor. Neoplasms may be benign, pre-malignant (carcinoma in situ) or malignant (cancer).

As used herein, and unless otherwise specified, "tumor" refers to all neoplastic cell growth and proliferation, whether malignant or benign, and all pre-cancerous and cancerous cells and tissues. As used herein, and unless otherwise specified, "neoplastic" refers to any form of deregulated or unregulated cell growth, whether malignant or benign, resulting in abnormal tissue growth. Thus, "neoplastic cells" include malignant and benign cells having deregulated or unregulated cell growth.

As used herein, and unless otherwise specified, the terms "cancer" and "cancerous" refer to or describe the physiological condition in mammals that is typically characterized by unregulated cell growth. Examples of cancer include, but are not limited to, lymphoma, leukemia, and solid tumors, such as, for example, lung cancer. In one embodiment, the term "cancer" as used herein includes, but is not limited to, solid tumors and blood-borne tumors. The term "cancer" refers to disease of skin tissues, organs, blood, and vessels, including, but not limited to, cancers of the bladder, bone or blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, atypical meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karyotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, sceleroderma, cutaneous vasculitis, Langerhans cell histiocytosis, leiomyosarcoma, fibrodysplasia ossificans progressiva, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistant to chemotherapy or radiation.

As used herein, and unless otherwise specified, the term "proliferative" disorder or disease refers to unwanted cell proliferation of one or more subset of cells in a multicellular organism resulting in harm (i.e., discomfort or decreased life expectancy) to the multicellular organism. For example, as used herein, proliferative disorder or disease includes neoplastic disorders and other proliferative disorders.

As used herein, and unless otherwise specified, the term "relapsed" refers to a situation where a subject, that has had a remission of cancer after a therapy, has a return of cancer cells.

As used herein, and unless otherwise specified, the term "refractory" or "resistant" refers to a circumstance where a subject, even after intensive treatment, has residual cancer cells in the body.

As used herein, and unless otherwise specified, the term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired.

As used herein, and unless otherwise specified, the term "anticancer agent" or "cancer therapeutic agent" is meant to include histone deacetylase (HDAC) inhibitors, including, but not limited to, romidepsin, anti-proliferative agents and chemotherapeutic agents, including, but not limited to, anti-metabolites (e.g., 5-fluoro uracil, methotrexate, fludarabine, cytarabine (also known as cytosine arabinoside or Ara-C), and high dose cytarabine), antimicrotubule agents (e.g., vinca alkaloids, such as vincristine and vinblastine; and taxanes, such as paclitaxel and docetaxel), alkylating agents (e.g., mechlorethamine, chlorambucil, cyclophosphamide, melphalan, melphalan, ifosfamide, carmustine, azacitidine, decitabine, busulfan, cyclophosphamide, dacarbazine, ifos-famide, and nitrosoureas, such as carmustine, lomustine, bischloroethylnitrosurea, and hydroxyurea), platinum agents (e.g., cisplatin, carboplatin, oxaliplatin, satraplatin (JM-216), and CI-973), anthracyclines (e.g., doxorubicin and daunorubicin), antitumor antibiotics (e.g., mitomycin, bleo-mycin, idarubicin, adriamycin, daunomycin (also known as daunorubicin, rubidomycin, or cerubidine), and mitoxan-trone), topoisomerase inhibitors (e.g., etoposide and camp-tothecins), purine antagonists or pyrimidine antagonists (e.g., 6-mercaptopurine, 5-fluorouracil, cytarabine, clofara-bine, and gemcitabine), cell maturing agents (e.g., arsenic trioxide and tretinoin), DNA repair enzyme inhibitors (e.g., podophyllotoxines, etoposide, irinotecan, topotecan, and teniposide), enzymes that prevent cell survival (e.g., aspara-ginase and pegaspargase), histone deacetylase inhibitors (e.g., vorinostat), any other cytotoxic agents (e.g., estramus-tine phosphate, dexamethasone, prednimustine, and procar-bazine), hormones (e.g., dexamethasone, prednisone, meth-ylprednisolone, tamoxifen, leuprolide, flutamide, and megestrol), monoclonal antibodies (e.g., gemtuzumab ozo-gamicin, alemtuzumab, rituximab, and yttrium-90-ibritu-momab tiuxetan), immuno-modulators (e.g., thalidomide and lenalidomide), Bcr-Abl kinase inhibitors (e.g., AP23464, AZD0530, CGP76030, PD180970, SKI-606, imatinib, BMS354825 (dasatinib), AMN107 (nilotinib), and VX-680), hormone agonists or antagonists, partial agonists or partial antagonists, kinase inhibitors, surgery, radio-therapy (e.g., gamma-radiation, neutron bean radiotherapy, electron beam radiotherapy, proton therapy, brachytherapy, and systemic radioactive isotopes), endocrine therapy, bio-logical response modifiers (e.g., interferons, interleukins, and tumor necrosis factor), hyperthermia and cryotherapy, and agents to attenuate any adverse effects (e.g., antiemet-ics).

As used herein, and unless otherwise specified, the terms "co-administration" and "in combination with" include the administration of two or more therapeutic agents simulta-neously, concurrently or sequentially within no specific time limits unless otherwise indicated. In one embodiment, the agents are present in the cell or in the subject's body at the same time or exert their biological or therapeutic effect at the same time. In one embodiment, the therapeutic agents are in the same composition or unit dosage form. In other embodi-ments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), essentially concomitantly with, or subse-quent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

As used herein, and unless otherwise specified, the terms "composition," "formulation," and "dosage form" are intended to encompass products comprising the specified ingredient(s) (in the specified amounts, if indicated), as well as any product(s) which result, directly or indirectly, from combination of the specified ingredient(s) in the specified amount(s).

As used herein, and unless otherwise specified, the term "excipient" refers to a pharmacologically inactive substance used as a carrier for the active ingredient of a medication or as a bulking agent to allow for convenient and accurate dosage of an active ingredient.

As used herein, and unless otherwise specified, the term "pharmaceutically acceptable carrier," "pharmaceutically acceptable excipient," "physiologically acceptable carrier," or "physiologically acceptable excipient" refers to a phar-maceutically-acceptable material, composition, or vehicle, such as a liquid or solid filler, diluent, excipient, solvent, or encapsulating material. In one embodiment, each compo-nent is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other prob-lems or complications, commensurate with a reasonable benefit/risk ratio. In one embodiment, by "pharmaceutical" or "pharmaceutically acceptable" it is meant that any diluent(s), excipient(s) or carrier(s) in the composition, formulation, or dosage form are compatible with the other ingredient(s) and not deleterious to the recipient thereof. See, e.g., Remington, *The Science and Practice of Phar-macy,* 21st Edition; Lippincott Williams & Wilkins: Phila-delphia, Pa., 2005; *Handbook of Pharmaceutical Excipients,* 5th Edition; Rowe et al., ed., The Pharmaceutical Press and the American Pharmaceutical Association: 2005; and *Hand-book of Pharmaceutical Additives,* 3rd Edition; Ash and Ash ed., Gower Publishing Company: 2007; *Pharmaceutical Preformulation and Formulation,* Gibson ed., CRC Press LLC: Boca Raton, Fla., 2004.

As used herein, and unless otherwise specified, the term "pharmaceutically acceptable salts" is meant to include salts of active compounds which are prepared with relatively nontoxic acids. Acid addition salts can be obtained by contacting the neutral form of such compounds with a sufficient amount of the desired acid, either neat or in a suitable inert solvent. Examples of pharmaceutically accept-able acid addition salts include those derived from inorganic acids like hydrochloric, hydrobromic, nitric, carbonic, monohydrogencarbonic, phosphoric, monohydrogenphos-phoric, dihydrogenphosphoric, sulfuric, monohydrogensul-furic, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesul-fonic, p-tolylsulfonic, citric, tartaric, methanesulfonic, and the like. Also included are salts of amino acids such as arginate and the like, and salts of organic acids like glu-curonic or galactunoric acids and the like (see, for example, Berge, et al. (1977)*Pharm. Sci.* 66:1-19).

A pharmaceutically acceptable salt form of a compound can be prepared in situ during the final isolation and puri-fication of the compound, or separately by reacting the free base functionality with a suitable organic or inorganic acid. Examples of typical pharmaceutically acceptable, nontoxic acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods used in the art such as ion exchange. Other pharmaceutically acceptable salts can include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts can include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, and unless otherwise specified, the terms, "polymorphs" and "polymorphic forms" and related terms refer to one of a variety of different crystal structures that can be adopted by a particular compound. In some embodiments, polymorphs occur when a particular chemical compound can crystallize in more than one structural arrangement. Different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in determining bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or might be difficult to filter and wash free of impurities (i.e., particle shape and size distribution might be different between one polymorph relative to the other).

As used herein, and unless otherwise specified, the term, "solvate" refers to a crystal form of a substance which contains solvent.

As used herein, and unless otherwise specified, the term "hydrate" refers to a crystal form adopted by a particular compound in which either a stoichiometric or non-stoichiometric amount of water is incorporated into the crystal lattice.

As used herein, and unless otherwise specified, the term "prodrug" refers to structurally modified forms of the compound that readily undergo chemical changes under physiological conditions to provide the compound. Additionally, prodrugs can be converted to the compound by chemical or biochemical methods in an ex vivo environment. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity.

As used herein, and unless otherwise specified, the term "anhydrous" refers to a form of a compound that is substantially free of water. One of skill in the art will appreciate that an anhydrous solid can contain various amounts of residual water wherein that water is not incorporated in the crystalline lattice. Such incorporation of residual water can depend upon a compound's hygroscopicity and storage conditions.

As used herein, and unless otherwise specified, the term "isostructural" or "isostructure" refers to two or more solid forms of a compound containing essentially the same three-dimensional arrangement of geometrically similar structural units. In some embodiments, "isostructural" forms show with similar or identical unit cell dimensions, the same space group, and similar or identical atomic coordinates for common atoms. In some embodiments, "isostructural" forms have the same structure, but not the same cell dimensions nor the same chemical composition, and have comparable variability in their atomic coordinates to that of the cell dimensions and chemical composition.

As used herein, and unless otherwise specified, the term "lyophilize" refers to the process of isolating a solid substance from solution and/or removal of solvent. In some embodiments, this may be achieved by various techniques known to one of skill in the art, including, for example, evaporation (e.g., under vaccum, for example by rotary evaporation), freeze drying, and/or freezing the solution and vaporizing frozen solvent away under vacuum conditions, etc.

As used herein, and unless otherwise specified, the term "parenteral" includes subcutaneous, intravenous, intramuscular, intra-artricular, intra-synovial, intrasternal, intrathecal, intrahepatic, intralesional and intracranial injection or infusion techniques.

As used herein, and unless otherwise specified, the term "substantially free of" means containing no more than an insignificant amount. In some embodiments, a composition or preparation is "substantially free of" a recited element if it contains less than 5%, 4%, 3%, 2%, or 1%, by weight of the element. In some embodiments, the composition or preparation contains less than 0.9%, 0.8%, 0.7%, 0.6%, 0.5%, 0.4%, 0.3%, 0.2%, 0.1% or less of the recited element. In some embodiments, the composition or preparation contains an undetectable amount of the recited element.

As used herein, and unless otherwise specified, the expression "unit dose" refers to a physically discrete unit of a formulation appropriate for a subject to be treated (e.g., for a single dose); each unit containing a predetermined quantity of an active agent selected to produce a desired therapeutic effect (it being understood that multiple doses may be required to achieve a desired or optimum effect), optionally together with a pharmaceutically acceptable carrier, which may be provided in a predetermined amount. The unit dose may be, for example, a volume of liquid (e.g,. an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described infra. It will be understood, however, that the total daily usage of a formulation of the present disclosure will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

As used herein, and unless otherwise specified, a compound described herein is intended to encompass all possible stereoisomers, unless a particular stereochemistry is specified. Where structural isomers of a compound are interconvertible via a low energy barrier, the compound may exist as a single tautomer or a mixture of tautomers. This can take the form of proton tautomerism; or so-called valence tautomerism in the compound.

Romidepsin

Romidepsin is a natural product which was isolated from *Chromobacterium violaceum* by Fujisawa Pharmaceuticals (Published Japanese Patent Application Hei 7 (1995)-64872; and U.S. Pat. No. 4,977,138, issued Dec. 11, 1990, each of which is incorporated herein by reference). Various preparations and purifications of romidepsin are described in PCT Publication WO 02/20817, which is incorporated herein by reference.

Romidepsin is a bicyclic peptide consisting of four amino acid residues (D-valine, D-cysteine, dehydrobutyrine, and L-valine) and a novel acid (3-hydroxy-7-mercapto-4-heptenoic acid), which contains both amide and ester bonds. Romidepsin can be obtained from *C. violaceum* using fermentation. It can also be prepared by synthetic or semi-synthetic means. The total synthesis of romidepsin reported by Kahn et al. (*J. Am. Chem. Soc.* 118:7237-7238, 1996) involves 14 steps and yields romidepsin in 18% overall yield. The structure of romidepsin is shown below (formula I):

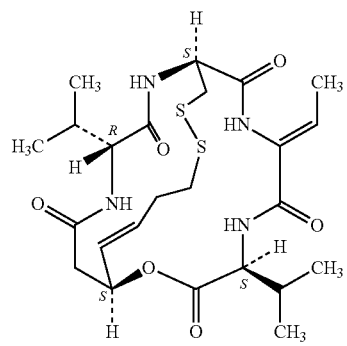

Romidepsin has been shown to have anti-microbial, immunosuppressive, and anti-tumor activities. In the US, it is approved for the treatment of patients with cutaneous T-cell lymphoma (CTCL) and peripheral T-cell lymphoma (PTCL). It is currently being tested for multiple myeloma and solid tumors (e.g., prostate cancer, pancreatic cancer, etc.) and is thought to act by selectively inhibiting deacetylases (e.g., histone deacetylase, tubulin deacetylase) (Nakajima et al., *Exp Cell Res* 241:126-133, 1998). One mode of action of romidepsin involves the inhibition of one or more classes of histone deacetylases (HDAC). Preparations and purification of romidepsin is described, for example, in U.S. Pat. No. 4,977,138 and International PCT Application Publication WO 02/20817, each of which is incorporated herein by reference.

Exemplary forms of romidepsin include, but are not limited to, salts, esters, pro-drugs, isomers, stereoisomers (e.g., enantiomers, diastereomers), tautomers, protected forms, reduced forms, oxidized forms, derivatives, and combinations thereof, with the desired activity (e.g., deacetylase inhibitory activity, aggressive inhibition, cytotoxicity). In certain embodiments, romidepsin is a pharmaceutical grade material and meets the standards of the U.S. Pharmacopoeia, Japanese Pharmacopoeia, or European Pharmacopoeia. In certain embodiments, the romidepsin is at least 95%, at least 98%, at least 99%, at least 99.9%, or at least 99.95% pure. In certain embodiments, the romidepsin is at least 95%, at least 98%, at least 99%, at least 99.9%, or at least 99.95% monomeric. In certain embodiments, no impurities are detectable in the romidepsin materials (e.g., oxidized material, reduced material, dimerized or oligomerized material, side products, etc.). Romidepsin typically includes less than 1.0%, less than 0.5%, less than 0.2%, or less than 0.1% of total other unknowns. The purity of romidepsin may be assessed by appearance, HPLC, specific rotation, NMR spectroscopy, IR spectroscopy, UV/Visible spectroscopy, powder x-ray diffraction (XRPD) analysis, elemental analysis, LC-mass spectroscopy, or mass spectroscopy.

In one embodiment, the formulation contains a derivative of romidepsin.

In one embodiment, the derivative of romidepsin is of the formula (II):

(II)

wherein
n is 1, 2, 3 or 4;
n is 0, 1, 2 or 3;
p and q are independently 1 or 2;
X is O, NH, or $NR_8$;
$R_1$, $R_2$, and $R_3$ are independently hydrogen, unsubstituted or substituted, branched or unbranched, cyclic or acyclic aliphatic; unsubstituted or substituted, branched or unbranched, cyclic or acyclic heteroaliphatic; unsubstituted or substituted aryl; or unsubstituted or substituted heteroaryl; and $R_4$, $R_5$, $R_6$, $R_7$ and $R_8$ are independently hydrogen, or substituted or unsubstituted, branched or unbranched, cyclic or acyclic aliphatic; and pharmaceutically acceptable forms thereof.

In one embodiment, m is 1, n is 1, p is 1, q is 1, X is O, $R_1$, $R_2$, and $R_3$ are unsubstituted or substituted, branched or unbranched acyclic aliphatic. In one embodiment, $R_4$, $R_5$, $R_6$ and $R_7$ are all hydrogen. In one embodiment, the derivative of romidepsin is of the formula (III):

(III)

wherein:
m is 1, 2, 3 or 4;
n is 0, 1, 2 or 3;
q is 2 or 3;
X is O, NH, or $NR_8$;
Y is $OR_8$, or $SR_8$;
$R_2$ and $R_3$ are independently hydrogen, unsubstituted or substituted, branched or unbranched, cyclic or acyclic aliphatic, unsubstituted or substituted, branched or unbranched, cyclic or acylic heteroaliphatic, unsubstituted or substituted aryl or unsubstituted or substituted heteroaryl;
$R_4$, $R_5$, $R_6$, $R_7$ and $R_8$ are independently selected from hydrogen or substituted or unsubstituted, branched or unbranched, cyclic or acyclic aliphatic, and pharmaceutically acceptable forms thereof.

In one embodiment, m is 1, n is 1, q is 2, X is NH and $R_2$ and $R_3$ are unsubstituted or substituted, branched or unbranched, acyclic aliphatic. In one embodiment, $R_4$, $R_5$, $R_6$ and $R_7$ are all hydrogen.

In one embodiment, the derivative of romidepsin is of the formula (IV):
wherein:

(IV)

A is a moiety that is cleaved under physiological conditions to yield a thiol group and includes, for example, an aliphatic or aromatic acyl moiety (to form a thioester bond), an aliphatic or aromatic thioxy (to form a disulfide bond), or the like, and pharmaceutically acceptable forms thereof. Such aliphatic or aromatic groups can include a substituted or unsubstituted, branched or unbranched, cyclic or acyclic aliphatic group, a substituted or unsubstituted aromatic group, a substituted or unsubstituted heteroaromatic group, or a substituted or unsubstituted heterocyclic group. A can be, for example, $—COR_1$, $—SC(=O)-O-R_1$, or $—SR_2$;

$R_1$ is independently hydrogen, substituted or unsubstituted amino, substituted or unsubstituted, branched or unbranched, cyclic or acyclic aliphatic, substituted or unsubstituted aromatic group, substituted or unsubstituted heteroaromatic group, or a substituted or unsubstituted heterocyclic group. In one embodiment, $R_1$ is hydrogen, methyl, ethyl, n-propyl, isopropyl, n-butyl, isobutyl, benzyl, or bromobenzyl;

$R_2$ is a substituted or unsubstituted, branched or unbranched, cyclic or acyclic aliphatic group, a substituted or unsubstituted aromatic group, a substituted or unsubstituted heteroaromatic group, or a substituted or unsubstituted heterocyclic group.

In one embodiment, $R_2$ is methyl, ethyl, 2-hydroxyethyl, isobutyl, a fatty acid, a substituted or unsubstituted benzyl, a substituted or unsubstituted aryl, cysteine, homocysteine, or glutathione.

In one embodiment, the derivatives of romidepsin are of formulae (V) or (V'):

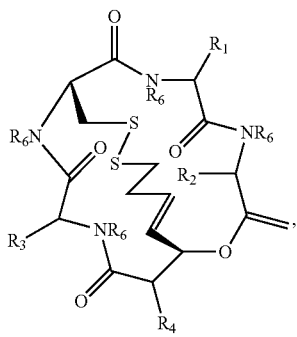

(V)

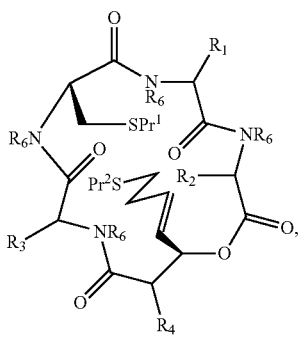

(V')

wherein:
each of $R_1$, $R_2$, $R_3$ and $R_4$ is the same or different and represent an amino acid side chain moiety;
each $R_6$ is the same or different and represents hydrogen or $(C_1-C_4)$alkyl; and
$Pr^1$ and $Pr^2$ are the same or different and represent hydrogen or thiol-protecting group.

In one embodiment, the amino acid side chain moieties are those derived from natural amino acids. In one embodiment, the amino acid side chain moieties are those derived from unnatural amino acids.

In one embodiment, each amino acid side chain is a moiety selected from hydrogen, $(C_1-C_6)$alkyl, $(C_2-C_6)$alkenyl, -L-O—C(0)-R', -L-C(0)-0-R'', -L-A, -L-NR''R''', -L-Het-C(0)-Het-R'', and -L-Het-R'', wherein L is a $(C_1-C_6)$ alkylene group, A is phenyl or a 5- or 6-membered heteroaryl group, each R' is the same or different and represents $(C_1-C_4)$alkyl, each R'' is the same or different and represent H or $(C_1-C_6)$alkyl, each -Het- is the same or different and is a heteroatom spacer selected from -0-, —N(R''')—, and —S—, and each R''' is the same of different and represents hydrogen or $(C_1-C_4)$alkyl.

In one embodiment, $R_6$ is hydrogen.
In one embodiment, $Pr^1$ and $Pr^2$ are the same or different and are selected from hydrogen and a protecting group selected from a benzyl group which is optionally substituted by $(C_1-C_6)$alkoxy, $(C_1-C_6)$acyloxy, hydroxy, nitro, picolyl, picolyl-N-oxide, anthrylmethyl, diphenylmethyl, phenyl, t-butyl, adamanthyl, $(C_1-C_6)$acyloxymethyl, $(C_1-C_6)$ alkoxymethyl, tetrahydropyranyl, benzylthiomethyl, phenylthiomethyl, thiazolidine, acetamidemethyl, benzamidomethyl, tertiary butoxycarbonyl (BOC), acetyl and its derivatives, benzoyl and its derivatives, carbamoyl, phenylcarbamoyl, and $(C_1-C_6)$alkylcarbamoyl.

Various romidepsin derivatives of formula (V) and (V') are disclosed in PCT application publication WO 2006/129105, published Dec. 7, 2006, which is incorporated herein by reference.

In one embodiment, a formulation of romidepsin is a liquid concentrate formulation for dilution. In some embodiments, provided are liquid formulations comprising one or more additional components. In some such embodiments, additional components are selected from the group consisting of, for example, solubilizers, stabilizers, buffers, tonicity modifiers, bulking agents, viscosity enhancers/reducers, surfactants, chelating agents, adjuvants, diluents, solvents, or other pharmaceutical additives.

In one embodiment, the additional component is a buffer. In one embodiment, the buffer is a citrate buffer. In another embodiment, the buffer is an acetate buffer.

Pharmaceutical Formulations

In one embodiment, provided herein are pharmaceutical formulations of romidepsin. In one embodiment, the formulation is a liquid concentrate formulation. In one embodiment, the formulation is a liquid concentrate formulation for dilution. In one embodiment, a liquid concentrate formulation for dilution is formulated in a solvent or a solvent system. In one embodiment, the solvent system comprises a citrate buffer. In another embodiment, the solvent system comprises an acetate buffer. In one embodiment, a romidepsin formulation is an injectable formulation.

In one embodiment, the romidepsin liquid concentrate for dilution is formulated in a solvent system. It was found that the solubility issues for developing a liquid IV formulation of romidepsin presented a problem. Romidepsin is practically insoluble in water. Therefore, solvent based formulations were explored. Solubility of romidepsin was studied in the following solvents and solvent mixtures: glycerin:EtOH (1:1); PEG 300; PEG 400; Tween 80:EtOH (1:1); dimethylacetamide (DMA); SolutolHS15:EtOH (1:1); NMP; Water; EtOH:PEG 400 (1:1); EtOH;water (4:6); EtOH; EtOH:PG (80:20); EtOH:PG (60:40); EtOH:PG (40:60); EtOH:PG (20:80); PG; EtOH:PG (40:60)+10% water; EtOH:PG (40:60)+butylated hydroxyanizole (BHA)/butylated hydroxytoluebe (BHT); and EtOH:PG (40:60)+ascorbic acid.

Solvents suitable for use in the formulations provided herein include, but are not limited to, propylene glycol (PG), ethanol (EtOH) and a buffer. In one embodiment, the buffer is a citrate buffer. In another embodiment, the buffer is an acetate buffer.

In one embodiment, the solvent system is a combination of 70% PG, 20% EtOH and 10% citrate buffer. In some embodiments, the solvent system comprises an organic acid, in particular a fatty acid. In a particular embodiment, the fatty acid is oleic acid. In one embodiment, the solvent system comprises 0.05% oleic acid. In another embodiment, the solvent system comprises 0.10% oleic acid. In yet another embodiment, the solvent system comprises 0.025% oleic acid.

In one embodiment, the solvent system is a combination of 30% PG, 30% EtOH and 40% acetate buffer. In another embodiment, the solvent system is a combination of 70% PG, 20% EtOH and 10% citrate buffer.

In one embodiment, a liquid concentrate formulation is diluted into normal saline.

In one embodiment, the pharmaceutical formulations provided herein may be formulated in various dosage forms for parenteral administration. In one embodiment, the pharmaceutical formulation provided herein may be provided in a unit-dosage form or multiple-dosage form. A unit-dosage form, as used herein, refers to a physically discrete unit suitable for administration to human and animal subjects, and packaged individually as is known in the art. Each unit-dose contains a predetermined quantity of the active ingredient(s) sufficient to produce the desired therapeutic effect, in association with the required pharmaceutical carriers or excipients. Examples of a unit-dosage form include an ampoule, a vial, a prefilled syringe, a cartridge, or an IV bag. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial.

In one embodiment, the pharmaceutical formulations provided herein may be administered at once or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

Parenteral Administration

In one embodiment, the pharmaceutical formulations provided herein may be administered parenterally by injection or infusion, for local or systemic administration. Parenteral administration, as used herein, include intravenous, intra-arterial, intraperitoneal, intrathecal, intraventricular, intraurethral, intrasternal, intracranial, intramuscular, intrasynovial, and subcutaneous administration.

In one embodiment, the pharmaceutical formulations provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, e.g., Remington, *The Science and Practice of Pharmacy*, supra).

In one embodiment, the pharmaceutical formulations intended for parenteral administration may include one or more pharmaceutically acceptable carriers and excipients, including, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

In one embodiment, suitable aqueous vehicles include, but are not limited to, water, saline, physiological saline or phosphate buffered saline (PBS), citrate buffer, acetate buffer, sodium chloride injection, Ringers injection, isotonic dextrose injection, sterile water injection, dextrose and lactated Ringers injection.

Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil.

Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

In one embodiment, suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid.

Suitable isotonic agents include, but are not limited to, sodium chloride, glycerin, and dextrose.

Suitable buffering agents include, but are not limited to, phosphate, acetate and citrate.

Suitable antioxidants include, but are not limited to, bisulfate and sodium metabisulfite.

Suitable local anesthetics include, but are not limited to, procaine hydrochloride.

Suitable suspending and dispersing agents include, but are not limited to, sodium carboxymethylcelluose, hydroxypropyl methylcellulose, and polyvinylpyrrolidone.

Suitable emulsifying agents include, but are not limited to, polyoxyethylene sorbitan monolaurate, polyoxyethylene sorbitan monooleate 80, and triethanolamine oleate.

Suitable sequestering or chelating agents include, but are not limited to, EDTA.

Suitable pH adjusting agents include, but are not limited to, sodium hydroxide, hydrochloric acid, acetic acid, citric acid, lactic acid, and sodium citrate.

Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

In one embodiment, a vehicle suitable for a liquid concentrate romidepsin formulation is propylene glycol (70): ethanol (20): citrate buffer (10) (pH-3.0; 25 mM). In one embodiment, a vehicle suitable for a liquid concentrate romidepsin formulation is propylene glycol (70): ethanol (20): acetate buffer (10) (pH-3.0; 25 mM).

In one embodiment, the pharmaceutical formulations provided herein are formulated for single or multiple dosage administration. In one embodiment, the single dosage formulations are packaged in an ampoule, a vial, or a syringe. In one embodiment, the multiple dosage formulations are packaged in a vial. In one embodiment, the multiple dosage parenteral formulations contain an antimicrobial agent at bacteriostatic or fungistatic concentrations. All parenteral formulations are sterile, as known and practiced in the art.

In one embodiment, the pharmaceutical formulations are provided as ready-to-use sterile solutions. In another embodiment, the pharmaceutical formulations are provided as sterile dry soluble products, including lyophilized powders to be reconstituted with a vehicle prior to use.

Combination Therapy

In some embodiments, romidepsin is administered in combination with one or more other pharmaceutical agents. In some embodiments, romidepsin is administered in combination with one or more other chemotherapeutic agents and/or in combination with one or more other pharmaceutical agents (e.g., pain relievers, anti-inflammatories, antibiotics, steroidal agents, anti-folates, kinase inhibitors, methyl transferase inhibitors, antibodies, etc.).

In certain embodiments, romidepsin is administered in combination with one or more cytotoxic agents. Exemplary cytotoxic agents include, but are not limited to, gemcitabine, decitabine, and flavopiridol. In certain embodiments, romidepsin is administered in combination with one or more taxanes and/or one or more proteasome inhibitors. Exemplary proteasome inhibitors include, but are not limited to, bortezomib (VELCADE®), peptide boronates, salinosporamide A (NPI-0052), lactacystin, epoxomicin (Ac(Me)-Ile-Ile-Thr-Leu-EX), MG-132 (Z-Leu-Leu-Leu-al), PR-171, PS-519, eponemycin, aclacinomycin A, CEP-1612, CVT-63417, PS-341 (pyrazylcarbonyl-Phe-Leu-boronate), PSI (Z-Ile-Glu(OtBu)-Ala-Leu-al), MG-262 (Z-Leu-Leu-Leu-bor), PS-273 (MNLB), omuralide (clasto-lactacystin-β-lactone), NLVS (Nip-Leu-Leu-Leu-vinyl sulfone), YLVS (Tyr-Leu-Leu-Leu-vs), dihydroeponemycin, DFLB (dansyl-Phe-Leu-boronate), ALLN (Ac-Leu-Leu-Nle-al), 3,4-dichloroisocoumarin, 4-(2-aminoethyl)-benzenesulfonyl fluoride, TMC-95A, gliotoxin, EGCG ((-)-epigallocatechin-3-gallate), YU101 (Ac-hFLFL-ex), and combinations thereof.

In certain embodiments, romidepsin is administered in combination with one or more anti-folates. In some such embodiments, romidepsin is administered in combination with one or more of: folinic acid (leucovorin), methotrexate, pralatrexate, premextred, triazinate, or combinations thereof.

In certain embodiments, romidepsin is administered in combination with one or more kinase inhibitors (e.g., tyrosine kinase inhibitors). In some embodiments, romidepsin is administered in combination with one or more antibodies that act as a kinase inhibitor. In some embodiments, romidepsin is administered in combination with one or more of ABT-869, AC220, AZD7762, BIBW 2992, BMS-690154, CDKIAT7519, CYC116, ISIS3521, GSK690693, GSK-461364, MK-0457, MLN8054, MLN8237, MP470, ON 01910.Na, OSI-930, PHA-739358, R935788, SNS-314, TLN-232, XL147, XL228, XL281, XL418, or XL765.

In certain embodiments, romidepsin is administered in combination with one or more methyl transferase inhibitors.

In certain embodiments, romidepsin is administered in combination with one or more therapeutic antibodies. In some embodiments, the therapeutic antibodies include, but are not limited to, bevacizumab, cetuximab, dasatinib, erlotinib, geftinib, imatinib, lapatinib, nilotinib, panitumumab, pegaptanib, ranibizumab, sorafenib, sunitinib, trastuzumab, or any antibody that binds to an antigen bound by one of these moieties.

In some embodiments, romidepsin is administered in combination with an anti-inflammatory agent, pain reliever, anti-nausea medication, or anti-pyretic. Anti-inflammatory agents useful in the methods provided herein include, but are not limited to, aspirin, ibuprofen, and acetaminophen.

In certain embodiments, romidepsin is administered in combination with a steroidal agent. In certain embodiments, romidepsin is administered in combination with a steroidal agent selected from the group consisting of alclometasone diprionate, amcinonide, beclomethasone diprionate, betamethasone, betamethasone benzoate, betamethasone diprionate, betamethasone sodium phosphate, betamethasone sodium phosphate and acetate, betamethasone valerate, clobetasol prorionate, clocortolone pivalate, cortisol (hydrocortisone), cortisol (hydrocortisone) acetate, cortisol (hydrocortisone) butyrate, cortisol (hydrocortisone) cypionate, cortisol (hydrocortisone) sodium phosphate, cortisol (hydrocortisone) sodium succinate, cortisol (hydrocortisone) valerate, cortisone acetate, desonide, desoximetasone, dexamethasone, dexamethasone acetate, dexamethasone sodium phosphate, diflorasone diacetate, fludrocortisone acetate, flunisolide, fluocinolone acetonide, fluocinonide, fluorometholone, flurandrenolide, halcinonide, medrysone, methylprednisolone, methylprednisolone acetate, methylprednisolone sodium succinate, mometasone furoate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, or combinations thereof. In one embodiment, romidepsin is administered in combination with dexamethasone.

In certain embodiments, romidepsin is administered in combination with an agent to treat gastrointestinal disturbances such as nausea, vomiting, and diarrhea. Such agents include, but are not limited to, anti-emetics, anti-diarrheals, fluid replacements, electrolyte replacements, etc.

In certain embodiments, romidepsin is administered in combination with electrolyte replacement or supplementation such as potassium, magnesium, or calcium. In certain embodiments, romidepsin is administered in combination with electrolyte replacement or supplementation such as potassium, and/or magnesium.

In certain embodiments, romidepsin is administered in combination with an anti-arrhythmic agent.

In certain embodiments, romidepsin is administered in combination with an agent that increases the production of platelets.

In certain embodiments, romidepsin is administered in combination with an agent to boost the production of blood cells. In certain embodiments, the agent is erythropoietin.

In some embodiments, romidepsin is administered in combination with an agent to prevent hyperglycemia.

In certain embodiments, romidepsin is administered with another HDAC or DAC inhibitor.

Methods Of Use

In one embodiment, provided is a method for treating, preventing, or managing cancer in a patient comprising administering to said patient an effective amount of a liquid concentrate formulation provided herein.

In some embodiments, cancers treatable by the methods provided herein include, but are not limited to, carcinomas, sarcomas, haematological malignancies and the like. In certain embodiments, cancer is a hematological malignancy. In certain embodiments, cancer is a solid tumor.

In one embodiment, hematological malignancies that can be treated by the methods provided herein include, but are not limited to, lymphomas, leukemias, multiple myeloma, plasma cell-derived cancers, relapsed hematological malignancies, and refractory hematological malignancies. In one embodiment, lymphomas that can be treated by the methods provided herein include, but are not limited to, mature B-cell lymphomas, mature T-cell and natural killer cell lymphomas, Hodgkin's lymphomas and immunodeficiency-associated lymphoproliferative disorders. In another embodiment, lymphomas that can be treated by the methods provided herein include, but are not limited to, small lymphocytic lymphoma, follicular lymphoma, Mantle cell lymphoma, diffuse large B-cell lymphoma, Burkitt lymphoma, B-cell lymphoblastic lymphoma, small cleaved B-cell lymphoma, non-cleaved B-cell lymphoma, cutaneous T-cell lymphoma (CTCL), and peripheral T-cell lymphoma (PTCL). In another embodiment, leukemias that can be treated by the methods provided herein include, but are not limited to, acute lymphoid leukemia (ALL), chronic lymphocytic leukemia (CLL), acute myeloid leukemia (AML), chronic myeloid leukemia (CIVIL), MLL-rearranged ALL, including leukemias that are relapsed, refractory or resistant to conventional therapy, multiple myeloma, and plasma cell-derived cancer.

In one embodiment, solid cancers that can be treated by the methods provided herein include, but are not limited to, cancer of the skin; lymph node; breast; cervix; uterus; gastrointestinal tract; pancreas, lung; ovary; prostate; colon; rectal; mouth; brain; head and neck; throat; testes; kidney;

pancreas; bone; spleen; liver; bladder; larynx; or nasal passages, and relapsed or refractory cancer.

In one embodiment, an effective amount of romidepsin to be used is a therapeutically effective amount. In one embodiment, the amounts of romidepsin to be used in the methods provided herein include an amount sufficient to cause improvement in at least a subset of patients with respect to symptoms, overall course of disease, or other parameters known in the art. Precise amounts for therapeutically effective amounts of romidepsin in the pharmaceutical compositions will vary depending on the age, weight, disease, and condition of the patient.

In one embodiment, romidepsin is administered intravenously. In one embodiment, romidepsin is administered intravenously over a 1-6 hour period. In one embodiment, romidepsin is administered intravenously over a 3-4 hour period. In one embodiment, romidepsin is administered intravenously over a 5-6 hour period. In one embodiment, romidepsin is administered intravenously over a 4 hour period.

In one embodiment, romidepsin is administered in a dose ranging from 0.5 mg/m$^2$ to 28 mg/m$^2$. In one embodiment, romidepsin is administered in a dose ranging from 0.5 mg/m$^2$ to 5 mg/m$^2$. In one embodiment, romidepsin is administered in a dose ranging from 1 mg/m$^2$ to 25 mg/m$^2$. In one embodiment, romidepsin is administered in a dose ranging from 1 mg/m$^2$ to 20 mg/m$^2$. In one embodiment, romidepsin is administered in a dose ranging from 1 mg/m$^2$ to 15 mg/m$^2$. In one embodiment, romidepsin is administered in a dose ranging from 2 mg/m$^2$ to 15 mg/m$^2$. In one embodiment, romidepsin is administered in a dose ranging from 2 mg/m$^2$ to 12 mg/m$^2$. In one embodiment, romidepsin is administered in a dose ranging from 4 mg/m$^2$ to 12 mg/m$^2$. In one embodiment, romidepsin is administered in a dose ranging from 6 mg/m$^2$ to 12 mg/m$^2$. In one embodiment, romidepsin is administered in a dose ranging from 8 mg/m$^2$ to 12 mg/m$^2$. In one embodiment, romidepsin is administered in a dose ranging from 8 mg/m$^2$ to 10 mg/m$^2$. In one embodiment, romidepsin is administered in a dose of about 8 mg/m$^2$. In one embodiment, romidepsin is administered in a dose of about 9 mg/m$^2$. In one embodiment, romidepsin is administered in a dose of about 10 mg/m$^2$. In one embodiment, romidepsin is administered in a dose of about 11 mg/m$^2$. In one embodiment, romidepsin is administered in a dose of about 12 mg/m$^2$. In one embodiment, romidepsin is administered in a dose of about 13 mg/m$^2$. In one embodiment, romidepsin is administered in a dose of about 14 mg/m$^2$. In one embodiment, romidepsin is administered in a dose of about 15 mg/m$^2$.

In one embodiment, romidepsin is administered in a dose of 14 mg/m$^2$ over a 4 hour iv infusion on days 1, 8 and 15 of the 28 day cycle. In one embodiment, the cycle is repeated every 28 days.

In one embodiment, increasing doses of romidepsin are administered over the course of a cycle. In one embodiment, the dose of about 8 mg/m$^2$ followed by a dose of about 10 mg/m$^2$, followed by a dose of about 12 mg/m$^2$ is administered over a cycle.

In some embodiments, unit doses of romidepsin are within the range of about 0.5 mg/m$^2$ to about 28 mg/m$^2$. In certain embodiments, unit doses are in the range of about 1 mg/m$^2$ to about 25 mg/m$^2$. In certain embodiments, unit doses are in the range of about 0.5 mg/m$^2$ to about 15 mg/m$^2$. In certain embodiments, the range of about 1 mg/m$^2$ to about 15 mg/m$^2$. In certain embodiments, unit doses are in the range of about 1 mg/m$^2$ to about 8 mg/m$^2$. In certain embodiments, unit doses are in the range of about 0.5 mg/m$^2$ to about 5 mg/m$^2$. In certain embodiments, the unit doses are in the range of about 2 mg/m$^2$ to about 10 mg/m$^2$. In some embodiments, unit doses are in the range of about 10 mg/m$^2$ to about 20 mg/m$^2$. In certain embodiments, unit doses are in the range of about 5 mg/m$^2$ to about 10 mg/m$^2$. In some embodiments, unit doses are in the range of about 10 mg/m$^2$ to about 15 mg/m$^2$. In some embodiments, unit doses are in the range of about 6 to about 19 mg/m$^2$. In some embodiments, unit doses are approximately 8 mg/m$^2$. In still other embodiments, the unit doses are approximately 9 mg/m$^2$. In still other embodiments, unit doses are approximately 10 mg/m$^2$. In still other embodiments, unit doses are approximately 11 mg/m$^2$. In still other embodiments, unit doses are approximately 12 mg/m$^2$. In still other embodiments, unit doses are approximately 13 mg/m$^2$. In still other embodiments, unit doses are approximately 14 mg/m$^2$. In still other embodiments, unit doses are approximately 15 mg/m$^2$. In still other embodiments, unit doses are approximately 30 mg/m$^2$.

In certain embodiments, different individual unit doses within the romidepsin therapy regimen are different. In some embodiments, increasing doses of romidepsin are administered over the course of a cycle. In certain embodiments, a dose of approximately 8 mg/m$^2$ is administered, followed by a dose of approximately 10 mg/m$^2$, followed by a dose of approximately 12 mg/m$^2$ may be administered over a cycle.

An amount of romidepsin administered in individual unit doses varies depending on the form of romidepsin being administered. In certain embodiments, individual unit doses of romidepsin are administered on one day followed by several days on which romidepsin is not administered. In certain embodiments, romidepsin is administered twice a week. In certain embodiments, romidepsin is administered once a week. In other embodiments, romidepsin is administered every other week.

In some embodiments, romidepsin is administered daily (for example for 2 weeks), twice weekly (for example for 4 weeks), thrice weekly (for example for 4 weeks), or on any of a variety of other intermittent schedules (e.g., on days 1, 3, and 5; on days 4 and 10; on days 1 and 15; on days 5 and 12; or on days 5, 12, and 19 of 21 or 28 day cycles).

In certain embodiments, romidepsin is administered on days 1, 8, and 15 of a 28 day cycle. In certain particular embodiments, an 8 mg/m$^2$ dose of romidepsin is administered on day 1, a 10 mg/m$^2$ dose of romidepsin is administered on day 8, and a 12 mg/m$^2$ dose of romidepsin is administered on day 15. In certain embodiments, romidepsin is administered on days 1 and 15 of a 28 day cycle with day 8 being skipped. A 28 day dosing cycle may be repeated. In certain embodiments, a 28 day cycle is repeated 2-10, 2-7, 2-5, or 3-10 times. In certain embodiments, the treatment includes 5 cycles. In certain embodiments, the treatment includes 6 cycles. In certain embodiments, the treatment includes 7 cycles. In certain embodiments, the treatment includes 8 cycles. In certain embodiments, 10 cycles are administered. In certain embodiments, greater than 10 cycles are administered.

Dosing

In some embodiments, romidepsin and/or compositions comprising romidepsin are administered according to a standard dosing regimen. In some embodiments, romidepsin and/or compositions comprising romidepsin are administered according to an accelerated dosing regimen.

Standard Dosing for Romidepsin

In some embodiments, unit doses of romidepsin are within the range of about 0.5 mg/m$^2$ to about 28 mg/m$^2$ body surface area. In some embodiments, the range of about 6 to about 18 mg/m² is used. In some embodiments, the range is about 10 mg/m² to about 17 mg/m². In some embodiments, particular unit doses are 10 mg/m², 12 mg/m², 13 mg/m², 14 mg/m², and 15 mg/m².

In some embodiments, intravenous dosing regimens include daily dosing for 2 weeks, twice weekly dosing for 4 weeks, thrice weekly dosing for 4 weeks, and various other intermittent schedules (e.g., on days 1, 3, and 5; on days 4 and 10; on days 1, 8 and 15; on days 1 and 15; on days 5 and 12; or on days 5, 12, and 19 of 21 or 28 day cycles).

In some embodiments, romidepsin is administered in individual unit doses over 4 hours on days 1, 8, and 15, with courses repeating every 28 days. Often, several courses (e.g., at least 4, at least 6, or more) are administered. Indeed, instances have been reported of as many as 72 courses being administered. In some embodiments, individual unit doses are administered by 4 hour infusion.

Accelerated Dosing for Romidepsin

Accelerated dosing regimens for romidepsin may be utilized, in which one or more individual unit doses is administered intravenously over a period of time that is less than or equal to about one hour. In some embodiments, one or more individual doses are administered intravenously over a period of time that is less than about 50 minutes, 40 minutes, 30 minutes, 20 minutes, or less. Any regimen that includes at least one unit dose administered over a period of time that is less than about one hour (60 minutes) may be considered an accelerated dosing regimen in accordance with the present disclosure.

In some embodiments, all unit doses within a regimen are administered intravenously over a time period that is less than or equal to about one hour. In some embodiments, only some of the unit doses within a regimen are administered over a time period that is less than or equal to about one hour. In some embodiments, one or more unit doses within a regimen are administered by a route other than intravenous administration (e.g., oral, subcutaneous, nasal, topical, etc.).

Accelerated dosing regimens of romidepsin can be administered without a significant increase in toxicity or adverse events, particularly in serious adverse events, as compared with a comparable regimen (e.g., an otherwise identical regimen) in which individual unit doses are administered intravenously over a 4-hour period. In one embodiment, accelerated dosing regimens can be administered without a significant increase in toxicity or adverse events, particularly in serious adverse events, as compared with a standard regimen of romidepsin administered by 4-hour intravenous infusion of a dose of about 6-14 mg/m² on days 1, 8, and 15 of a 28 day cycle.

In some embodiments, romidepsin is administered in an accelerated dosing regimen that is identical to a standard dosing regimen except that one or more unit doses is administered over a time period that is less than about 1 hour (e.g., rather than over a time period of about 4 hours).

As will be appreciated by one of skill in the art, the dosage, timing and/or routes of administration of particular unit doses of romidepsin may vary depending on the patient and condition being treated. In certain embodiments, the cycles are continued as long as the patient is responding. Therapy may be terminated once there is disease progression, a cure or remission is achieved, or side effects become intolerable. Adverse side effects may also call for lowering the dosage of romidepsin administered, or for adjusting the schedule by which doses are administered.

Kits

In one embodiment, a kit comprises a dosage form of romidepsin liquid concentrate formulation for dilution. Kits can further comprise a pharmacologically active derivative of romidepsin.

In other embodiments, kits can further comprise devices that are used to administer the active ingredients. Examples of such devices include, but are not limited to, syringes, and drip bags.

In one embodiment, kits can further comprise a pharmaceutically acceptable vehicle that can be used to administer one or more active ingredients. For example, if an active ingredient is provided as sterile dry soluble products, including lyophilized powders to be reconstituted with a vehicle prior to use, the kit can comprise a sealed container of a suitable vehicle in which the active ingredient can be reconstituted to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Unless otherwise defined, all technical and scientific terms used herein are accorded the meaning commonly known to one of skill in the art. All publications, patents, published patent applications, and other references mentioned herein are hereby incorporated by reference in their entirety. The embodiments of the disclosure should not be deemed to be mutually exclusive and can be combined.

EXAMPLES

The following examples are provided by way of illustration, not limitation.

Example 1

Romidepsin Liquid Concentrate Injectable Formulations

Romidepsin liquid concentrate injectable formulation (citrate buffer) and romidepsin liquid concentrate injectable formulation (acetate buffer) were manufactured at the Celgene, Melrose Park, Ill. Pilot Laboratory using romidepsin raw material (Manufacturer: Sandoz). The product information for the two formulations is summarized in Table 1 (Citrate Buffer) and Table 2 (Acetate Buffer).

TABLE 1

| | |
|---|---|
| Product name | Romidepsin Injection (Citrate Buffer) |
| Strength | 5 mg Romidepsin/mL |
| Banch Size | 1 L |
| Vehicle | Propylene Glycol:Ethanol:Citrate buffer (pH 4.5, 25 mM) = 70:20:10 |
| Fill Volume Claim | 2 mL |
| Container and Closure | Vials, Schott, P.O. # BL-026545, Item # 5010-2095, Lot # 6102291228; Stoppers, Westar RS, 13 mm Teflon 4416/50; Grey; Caps 13 mm, light blue |
| RM (active) | Romidepsin |
| Excipient | Propylene Glycol, Ethanol, Citric Acid Anhydrous, |

TABLE 1-continued

Sodium Citrate Dihydrate

TABLE 2

| | |
|---|---|
| Product name | Romidepsin Injection (Acetate Buffer) |
| Strength | 5 mg Romidepsin/mL |
| Banch Size | 1 L |
| Vehicle | Propylene Glycol:Ethanol:Acetate buffer (pH 4.0, 25 mM) = 30:30:40 |
| Fill Volume Claim | 2 mL |
| Container and Closure | Vials, Schott, P.O. # BL-026545, Item # 5010-2095, Lot # 6102291228; Stoppers, Westar RS, 13 mm Teflon 4416/50; Grey; Caps 13 mm, light blue |
| RM (active) | Romidepsin |
| Excipient | Propylene Glycol, Ethanol, Acetic Acid Glacial |

Example 2

Stability of Romidepsin Liquid Concentrate Injectable Formulations

Storage Conditions

Finished romidepsin liquid concentrate injectable formulation (citrate buffer) and romidepsin liquid concentrate injectable formulation (acetate buffer) were injected in vials and stored inverted and upright per stability testing protocols in storage chambers maintained at −85° C. to −70° C. and −25° C. to −10° C., 5° C.±3° C., 25° C.±2° C./60% RH±5% RH, and 40° C.±2° C./75% RH±5% RH. A pre-determined number of vials was removed from storage after specified time periods for tersing.

Test Methods

The testing parameters included: visual appearance/color of solution, pH, romidepsin assay, individual impurities, and total impurities by HPLC.

Results

Based on formulation composition design of experiment study of the potentially promising compositions, five formulations were selected. The romidepsin liquid concentrate formulations were prepared at 100 mL batch size. Two mL aliquots of each formulation were filled into 2 mL clear ampoule vials and sealed. The compositions of romidepsin liquid concentrate injectable formulations are listed in Table 3.

TABLE 3

| | |
|---|---|
| Formulation 1 | Romidepsin 5 mg/mL<br>PG:EtOH:citrate buffer (pH 4.5; 25 mM)::70:20:10 with 0.05% oleic acid |
| Formulation 2 | Romidepsin 5 mg/mL<br>PG:EtOH:citrate buffer (pH 4.5; 25 mM)::70:20:10 |
| Formulation 3 | Romidepsin 5 mg/mL<br>PG:EtOH:citrate buffer (pH 4.5; 50 mM)::70:20:10 with 0.10% oleic acid |
| Formulation 4 | Romidepsin 5 mg/mL<br>PG:EtOH:acetate buffer (pH 4.0; 20 mM)::30:30:40 |
| Formulation 5 | Romidepsin 5 mg/mL<br>PG:EtOH:citrate buffer (pH 4.5; 25 mM)::70:20:10 with 0.025% oleic acid |

Table 4 shows the stability data of five romidepsin liquid concentrate injectable formulations stored at 5° C.

TABLE 4

| Samples stored at 5° C. | | LC (%) | Relative peak area @ RRT | | | | | | |
|---|---|---|---|---|---|---|---|---|---|
| | | | 0.34 | 0.45 | 1.00 | 1.36 | 1.89 | 2.04 | 2.85 |
| F1-1 | initial | 102.2 | | | 100.00 | | | | |
| | 1 M | 102.1 | | | 100.00 | | | | |
| | 2 M | 102.2 | | | 100.00 | | | | |
| | 3 M | 103.1 | | | 100.00 | | | | |
| | 6 M | 104.0 | | | 100.00 | | | | |
| F1-2 | initial | 103.8 | | | 100.00 | | | | |
| | 1 M | 102.4 | | | 100.00 | | | | |
| | 2 M | 103.1 | | | 100.00 | | | | |
| | 3 M | 103.1 | | | 100.00 | | | | |
| | 6 M | 105.3 | | | 100.00 | | | | |
| F2-1 | initial | 104.7 | | | 100.00 | | | | |
| | 1 M | 104.1 | | | 100.00 | | | | |
| | 2 M | 102.8 | | | 100.00 | | | | |
| | 3 M | 104.4 | | | 100.00 | | | | |
| | 6 M | 105.0 | | | 100.00 | | | | |
| F2-2 | initial | 104.7 | | | 100.00 | | | | |
| | 1 M | 103.9 | | | 100.00 | | | | |
| | 2 M | 103.6 | | | 100.00 | | | | |
| | 3 M | 104.7 | | | 100.00 | | | | |
| | 6 M | 106.1 | | | 100.00 | | | | |
| F3-1 | initial | 104.3 | | | 100.00 | | | | |
| | 1 M | 102.7 | | | 100.00 | | | | |
| | 2 M | 103.1 | | | 100.00 | | | | |
| | 3 M | 103.4 | | | 100.00 | | | | |
| | 6 M | 104.1 | | | 100.00 | | | | |
| F3-2 | initial | 103.2 | | | 100.00 | | | | |
| | 1 M | 103.2 | | | 100.00 | | | | |
| | 2 M | 102.6 | | | 100.00 | | | | |
| | 3 M | 103.6 | | | 100.00 | | | | |
| | 6 M | 104.4 | | | 100.00 | | | | |
| F4-1 | initial | 108.3 | | | 100.00 | | | | |
| | 1 M | 107.1 | | | 100.00 | | | | |
| | 2 M | 106.5 | | | 100.00 | | | | |
| | 3 M | 108.3 | | | 100.00 | | | | |
| | 6 M | 108.2 | | | 100.00 | | | | |
| F4-2 | initial | 108.4 | | | 100.00 | | | | |
| | 1 M | 107.0 | | | 100.00 | | | | |
| | 2 M | 106.5 | | | 100.00 | | | | |
| | 3 M | 107.7 | | | 100.00 | | | | |
| | 6 M | 108.4 | | | 100.00 | | | | |
| F5-1 | initial | 101.7 | | | 100.00 | | | | |
| | 1 M | 102.2 | | | 100.00 | | | | |
| | 2 M | 102.4 | | | 100.00 | | | | |
| | 3 M | 103.2 | | | 100.00 | | | | |
| | 6 M | 103.6 | | | 100.00 | | | | |
| F5-2 | initial | 102.7 | | | 100.00 | | | | |
| | 1 M | 102.4 | | | 100.00 | | | | |
| | 2 M | 102.1 | | | 100.00 | | | | |
| | 3 M | 103.6 | | | 100.00 | | | | |
| | 6 M | 103.7 | | | 100.00 | | | | |

Table 5 shows the stability data of five romidepsin liquid concentrate injectable formulations stored at controlled ambient temperature.

TABLE 5

| Samples stored at RT | | LC (%) | Relative peak area @ RRT | | | | | | |
|---|---|---|---|---|---|---|---|---|---|
| | | | 0.34 | 0.45 | 1.00 | 1.36 | 1.89 | 2.04 | 2.85 |
| F1-1 | initial | 102.2 | | | 100.00 | | | | |
| | 1 M | 103.8 | | | 100.00 | | | | |
| | 2 M | 103.9 | | | 100.00 | | | | |

TABLE 5-continued

| | | LC (%) | 0.34 | 0.45 | 1.00 | 1.36 | 1.89 | 2.04 | 2.85 |
|---|---|---|---|---|---|---|---|---|---|
| | 3 M | 104.2 | | | 100.00 | | | | |
| | 6 M | 105.7 | | | 100.00 | | | | |
| F1-2 | initial | 103.8 | | | 100.00 | | | | |
| | 1 M | 102.8 | | | 100.00 | | | | |
| | 2 M | 104.3 | | | 100.00 | | | | |
| | 3 M | 102.7 | | | 100.00 | | | | |
| | 6 M | 106.3 | | | 100.00 | | | | |
| F2-1 | initial | 104.7 | | | 100.00 | | | | |
| | 1 M | 103.5 | | | 100.00 | | | | |
| | 2 M | 104.3 | | | 100.00 | | | | |
| | 3 M | 104.1 | | | 100.00 | | | | |
| | 6 M | 107.4 | | | 100.00 | | | | |
| F2-2 | initial | 104.7 | | | 100.00 | | | | |
| | 1 M | 103.6 | | | 100.00 | | | | |
| | 2 M | 104.0 | | | 100.00 | | | | |
| | 3 M | 103.8 | | | 100.00 | | | | |
| | 6 M | 106.0 | | | 100.00 | | | | |
| F3-1 | initial | 104.3 | | | 100.00 | | | | |
| | 1 M | 103.6 | | | 100.00 | | | | |
| | 2 M | 103.4 | | | 100.00 | | | | |
| | 3 M | 103.9 | | | 100.00 | | | | |
| | 6 M | 104.6 | | | 100.00 | | | | |
| F3-2 | initial | 103.2 | | | 100.00 | | | | |
| | 1 M | 104.1 | | | 100.00 | | | | |
| | 2 M | 103.6 | | | 100.00 | | | | |
| | 3 M | 103.8 | | | 100.00 | | | | |
| | 6 M | 105.6 | | | 100.00 | | | | |
| F4-1 | initial | 108.3 | | | 100.00 | | | | |
| | 1 M | 108.2 | | | 100.00 | | | | |
| | 2 M | 107.9 | | | 100.00 | | | | |
| | 3 M | 108.0 | | | 100.00 | | | | |
| | 6 M | 110.0 | | | 100.00 | | | | |
| F4-2 | initial | 108.4 | | | 100.00 | | | | |
| | 1 M | 107.4 | | | 100.00 | | | | |
| | 2 M | 108.1 | | | 100.00 | | | | |
| | 3 M | 107.9 | | | 100.00 | | | | |
| | 6 M | 109.1 | | | 100.00 | | | | |
| F5-1 | initial | 101.7 | | | 100.00 | | | | |
| | 1 M | 103.2 | | | 100.00 | | | | |
| | 2 M | 103.0 | | | 100.00 | | | | |
| | 3 M | 103.4 | | | 100.00 | | | | |
| | 6 M | 104.9 | | | 100.00 | | | | |
| F5-2 | initial | 102.7 | | | 100.00 | | | | |
| | 1 M | 103.3 | | | 100.00 | | | | |
| | 2 M | 103.0 | | | 100.00 | | | | |
| | 3 M | 103.4 | | | 100.00 | | | | |
| | 6 M | 104.3 | | | 100.00 | | | | |

Table 6 shows the stability data of five romidepsin liquid concentrate injectable formulations stored at 40° C.

TABLE 6

| Samples stored at 40° C. | | LC | 0.34 | 0.37 | 0.45 | 0.53 | 0.60 | 0.67 | 1.00 | 1.36 | 1.89 | 2.04 | 2.85 |
|---|---|---|---|---|---|---|---|---|---|---|---|---|---|
| F1-1 | initial | 102.2 | | | | | | | 100.00 | | | | |
| | 1 M | 102.8 | | | | | | | 100.00 | | | | |
| | 2 M | 103.0 | | | | | | | 99.84 | | 0.07 | | 0.09 |
| | 3 M | 106.6 | 0.06 | | 0.04 | | | | 99.76 | | 0.04 | | 0.09 |
| | 6 M | 102.2 | 0.13 | 0.03 | 0.09 | | 0.04 | | 99.40 | | 0.09 | | 0.22 |
| F1-2 | initial | 103.8 | | | | | | | 100.00 | | | | |
| | 1 M | 103.0 | | | | | | | 100.00 | | | | |
| | 2 M | 110.4 | | | | | | | 99.91 | | 0.04 | | 0.06 |
| | 3 M | 103.3 | 0.03 | | 0.03 | | | | 99.78 | | 0.06 | | 0.10 |
| | 6 M | 113.2 | 0.28 | 0.05 | 0.19 | 0.07 | 0.09 | | 99.03 | | 0.06 | | 0.20 |
| F2-1 | initial | 104.7 | | | | | | | 100.00 | | | | |
| | 1 M | 103.5 | | | | | | | 100.00 | | | | |
| | 2 M | 103.5 | | | | | | | 99.91 | | 0.04 | | 0.05 |
| | 3 M | 103.6 | 0.04 | | 0.03 | | | | 99.79 | | 0.05 | | 0.10 |
| | 6 M | 103.0 | 0.15 | 0.05 | 0.09 | 0.03 | 0.05 | | 99.33 | | 0.09 | | 0.21 |
| F2-2 | initial | 104.7 | | | | | | | 100.00 | | | | |
| | 1 M | 103.1 | | | | | | | 100.00 | | | | |
| | 2 M | 105.9 | | | | | | | 99.89 | | 0.04 | | 0.07 |
| | 3 M | 103.4 | 0.04 | | 0.03 | | | | 99.78 | | 0.06 | | 0.10 |
| | 6 M | 103.9 | 0.13 | 0.03 | 0.08 | | 0.03 | | 99.43 | | 0.09 | | 0.20 |
| F3-1 | initial | 104.3 | | | | | | | 100.00 | | | | |
| | 1 M | 102.3 | | | | | | | 100.00 | | | | |
| | 2 M | 102.3 | | | | | | | 99.95 | | | | 0.05 |
| | 3 M | 103.2 | 0.04 | | 0.03 | | | | 99.82 | | 0.04 | | 0.07 |
| | 6 M | 102.5 | 0.15 | 0.05 | 0.09 | 0.03 | 0.05 | | 99.39 | | 0.07 | | 0.18 |
| F3-2 | initial | 103.2 | | | | | | | 100.00 | | | | |
| | 1 M | 102.9 | | | | | | | 100.00 | | | | |
| | 2 M | 103.4 | | | | | | | 99.92 | | 0.04 | | 0.04 |
| | 3 M | 103.0 | 0.03 | | 0.04 | | | | 99.81 | | 0.04 | | 0.07 |
| | 6 M | 102.6 | 0.15 | 0.05 | 0.10 | | 0.05 | | 99.37 | | 0.08 | | 0.18 |
| F4-1 | initial | 108.3 | | | | | | | 100.00 | | | | |
| | 1 M | 106.9 | | | | | | | 100.00 | | | | |
| | 2 M | 109.7 | | | | | | | 99.90 | | 0.04 | | 0.05 |
| | 3 M | 107.7 | | | | | | | 99.84 | | 0.08 | | 0.08 |
| | 6 M | 108.3 | | | | | | 0.04 | 99.64 | | 0.16 | | 0.16 |
| F4-2 | initial | 108.4 | | | | | | | 100.00 | | | | |
| | 1 M | 107.2 | | | | | | | 100.00 | | | | |
| | 2 M | 108.6 | | | | | | | 99.90 | | 0.05 | | 0.05 |

TABLE 6-continued

| Samples stored at 40° C. | | Relative peak area @ RRT | | | | | | | | | |
|---|---|---|---|---|---|---|---|---|---|---|---|
| | LC | 0.34 | 0.37 | 0.45 | 0.53 | 0.60 | 0.67 | 1.00 | 1.36 | 1.89 | 2.04 | 2.85 |
| 3 M | 107.4 | | | | | | | 99.88 | | 0.07 | | 0.05 |
| 6 M | 107.6 | | | | | | 0.03 | 99.68 | | 0.14 | | 0.15 |
| F5-1 initial | 101.7 | | | | | | | 100.00 | | | | |
| 1 M | 102.9 | | | | | | | 100.00 | | | | |
| 2 M | 103.9 | | | | | | | 99.95 | | | | 0.05 |
| 3 M | 102.1 | 0.03 | | 0.03 | | | | 99.81 | | 0.05 | | 0.08 |
| 6 M | 101.0 | 0.18 | | 0.11 | 0.04 | 0.07 | | 99.34 | | 0.08 | | 0.19 |
| F5-2 initial | 102.7 | | | | | | | 100.00 | | | | |
| 1 M | 103.0 | | | | | | | 100.00 | | | | |
| 2 M | 104.3 | | | | | | | 99.89 | | 0.04 | | 0.07 |
| 3 M | 102.4 | 0.03 | | | | | | 99.83 | | 0.06 | | 0.08 |
| 6 M | 101.6 | 0.16 | 0.05 | 0.11 | 0.03 | 0.07 | | 99.32 | | 0.08 | | 0.19 |

Table 7 shows the stability data of romidepsin liquid concentrate injectable formulations after exposure to light.

TABLE 7

| Stressed at RT under light | | | | | | | |
|---|---|---|---|---|---|---|---|
| | LC | Relative peak area @ RRT | | | | | |
| | (%) | 0.34 | 0.45 | 1.00 | 1.36 | 1.89 | 2.04 | 2.85 |
| F1 initial | 102.2 | | | 100.00 | | | | |
| 1 M | 102.4 | | | 100.0 | | | | |
| 2 M | 101.7 | | | 99.85 | | 0.05 | | 0.10 |
| 3 M | 102.4 | | | 99.70 | 0.03 | 0.08 | 0.03 | 0.14 |
| 6 M | 101.7 | | | 99.73 | | 0.09 | | 0.18 |
| F2 initial | 104.7 | | | 100.0 | | | | |
| 1 M | 102.8 | | | 100.0 | | | | |
| 2 M | 102.1 | | | 99.82 | | 0.07 | | 0.12 |
| 3 M | 103.4 | | | 99.66 | 0.02 | 0.11 | 0.02 | 0.18 |
| 6 M | 102.0 | | | 99.50 | 0.03 | 0.17 | | 0.29 |
| F3 initial | 104.3 | | | 100.0 | | | | |
| 1 M | 103.2 | | | 100.0 | | | | |
| 2 M | 101.7 | | | 99.83 | | 0.06 | | 012 |
| 3 M | 102.9 | | | 99.76 | 0.02 | 0.07 | 0.02 | 0.13 |
| 6 M | 102.1 | | | 99.78 | | 0.07 | | 0.14 |
| F4 initial | 108.3 | | | 100.0 | | | | |
| 1 M | 106.7 | | | 99.95 | | 0.05 | | |
| 2 M | 105.4 | | | 99.64 | | 0.16 | | 0.20 |
| 3 M | 107.0 | | | 99.57 | 0.04 | 0.17 | 0.02 | 0.20 |
| 6 M | 104.8 | | | 99.35 | 0.06 | 0.27 | | 0.33 |
| F5 initial | 101.7 | | | 100.0 | | | | |
| 1 M | 102.3 | | | 100.0 | | | | |
| 2 M | 101.7 | | | 99.83 | | 0.06 | | 0.11 |
| 3 M | 102.4 | | | 99.63 | 0.04 | 0.12 | 0.02 | 0.20 |
| 6 M | 100.8 | | | 99.55 | | 0.15 | | 0.30 |

No loss of potency was observed for all tested formulations over the stability test period as demonstrated by the consistency of the % label claim results. Individual related substances were found to be less than 0.05% or not detected at all time points up to 6 months at 5° C. and controlled ambient conditions. A few related substances were observed with the stability samples under accelerated conditions at 40° C. The highest level of related substance observed was no more than 0.30% at 6 months at 40° C. Samples exposed to light showed higher levels of related substances when compoared with samples stores in dark at controlled ambient temperature.

Dilution study was performed to evaluate the compatibility of the tested formulations with normal saline. A dose of 22.5 mg (4.5 mL of formulation) was diluted into 250 mL of normal saline. After gentle mixing, the diluted formulation was observed for appearance. Formulations with oleic acid as a component (formulations 1, 3 and 5) showed haziness in the diluted samples while formulations without oleic acid (formulations 2 and 4) appeared clear. These results indicate that the romidepsin liquid concentrate injectable formulations 2 and 4 are compatible with normal saline upon dilution and were used for further studies.

Summary of stability test results for romidepsin liquid concentrate injection in citrate buffer (formulation 2) and romidepsin liquid concentrate injection in acetate buffer (formulation 4) are shown in Tables 8-15.

Tables 8 and 9 demonstrate test results for romidepsin liquid concentrate injection in citrate buffer and romidepsin liquid concentrate injection in acetate buffer stored at −85° C. to −70° C. and at −25° C. to −10° C. up to 1 month, accordingly.

TABLE 8

| | Citrate | | | | | | Acetate | | | | | |
|---|---|---|---|---|---|---|---|---|---|---|---|---|
| | Upright | | | Inverted | | | Upright | | | Inverted | | |
| n = 2 | 0 | 1 W | 1 M | 0 | 1 W | 1 M | 0 | 1 W | 1 M | 0 | 1 W | 1 M |
| Label Claim (%) | 103.5 | 104.1 | 104.8 | 103.5 | 104.1 | 105.0 | 105.2 | 107.4 | 107.7 | 105.2 | 107.4 | 108.0 |
| Impurities (%) | | | | | | 0.09 | | | | | | |
| Total Impurities (%) | | | | | | 0.09 | | | | | | |
| Appearance | Sample solution is transparent, no visible particulate matter | | | | | | | | | | | |
| pH | 4.5 | 4.6 | 4.7 | 4.5 | 4.7 | 4.7 | 4.0 | 4.1 | 4.1 | 4.0 | 4.1 | 4.1 |

TABLE 9

|  | Citrate | | | | | | Acetate | | | | | |
| --- | --- | --- | --- | --- | --- | --- | --- | --- | --- | --- | --- | --- |
|  | Upright | | | Inverted | | | Upright | | | Inverted | | |
| n = 2 | 0 | 1 W | 1 M | 0 | 1 W | 1 M | 0 | 1 W | 1 M | 0 | 1 W | 1 M |
| Label Claim (%) | 103.5 | 104.8 | 104.8 | 103.5 | 101.7 | 104.1 | 105.2 | 107.5 | 108.2 | 105.2 | 107.9 | 107.7 |
| Impurities (%) |  |  |  |  |  | 0.09 |  |  |  |  |  |  |
| Total Impurities (%) |  |  |  |  |  | 0.09 |  |  |  |  |  |  |
| Appearance | Sample solution is transparent, no visible particulate matter | | | | | | | | | | | |
| pH | 4.5 | 4.7 | 4.7 | 4.5 | 4.7 | 4.7 | 4.0 | 4.1 | 4.2 | 4.0 | 4.1 | 4.2 |

Tables 10 and 11 show the test results for romidepsin liquid concentrate injection in citrate buffer (Table 10) and romidepsin liquid concentrate injection in acetate buffer (Table 11) stored at 5° C.±3° C. up to 12 months.

TABLE 10

|  | Citrate | | | | | | | | | | | |
| --- | --- | --- | --- | --- | --- | --- | --- | --- | --- | --- | --- | --- |
|  | Upright | | | | | | Inverted | | | | | |
| n = 2 | 0 | 1 M | 3 M | 6 M | 9 M | 12 M | 0 | 1 M | 3 M | 6 M | 9 M | 12 M |
| Label Claim (%) | 103.5 | 105.0 | NA | 102.6 | NA | 104.7 | 103.5 | 105.7 | 105.7 | 103.5 | 103.3 | 105.0 |
| Impurities (%)[1] | 0.09 | 0.09 | NA | 0.09 | NA | 0.09 | 0.09 | 0.09 | 0.09 | 0.10 | 0.09 | 0.10 |
| Total Impurities (%) | 0.09 | 0.09 | NA | 0.09 | NA | 0.09 | 0.09 | 0.09 | 0.09 | 0.10 | 0.09 | 0.10 |
| Appearance | Sample solution is transparent, no visible particulate matter | Sample solution is transparent, no visible particulate matter | NA | Sample solution is transparent, no visible particulate matter | NA | Clear solution, no visible particulate matter | Sample solution is transparent, no visible particulate matter | | | | Clear solution, no visible particulate matter | |
| pH | 4.5 | 4.7 | NA | 4.7 | NA | 4.5 | 4.5 | 4.7 | 4.6 | 4.7 | 4.6 | 4.5 |

TABLE 11

|  | Acetate | | | | | | | | | | | |
| --- | --- | --- | --- | --- | --- | --- | --- | --- | --- | --- | --- | --- |
|  | Upright | | | | | | Inverted | | | | | |
| n = 2 | 0 | 1 M | 3 M | 6 M | 9 M | 12 M | 0 | 1 M | 3 M | 6 M | 9 M | 12 M |
| Label Claim (%) | 105.2 | 107.8 | NA | 107.9 | NA | 108.6 | 105.2 | 108.2 | 110.1 | 108.1 | 107.1 | 108.2 |
| Impurities (%) | 0.09 | 0.09 | NA | 0.10 | NA | 0.09 | 0.09 | 0.09 | 0.09 | 0.10 | 0.09 | 0.09 |
| Total Impurities (%) | 0.09 | 0.09 | NA | 0.10 | NA | 0.09 | 0.09 | 0.09 | 0.09 | 0.10 | 0.09 | 0.09 |
| Appearance | Sample solution is transparent, no visible particulate matter | Sample solution is transparent, no visible particulate matter | NA | Sample solution is transparent, no visible particulate matter | NA | Clear solution, no visible particulate matter | Sample solution is transparent, no visible particulate matter | | | | Clear solution, no visible | |
| pH | 4.0 | 4.2 | NA | 4.1 | NA | 4.0 | 4.0 | 4.3 | 4.1 | 4.1 | 4.1 | 4.0 |

As can be seen, romidepsin liquid concentrate injection in citrate buffer and romidepsin liquid concentrate injection in acetate buffer maintained physical and chemical stabilities at −85° C. to −70° C. for up to 1 month (Table 8), at −25° C. to −10° C. for up to 1 month (Table 9), and at 5° C.±3° C. up to 12 months (Tables 10 and 11).

Table 12 demonstrates the test results for romidepsin liquid concentrate injection in citrate buffer stored at 25° C.±2° C./60% RH±5% RH.

The results demonstrate that the romidepsin formulation in acetate buffer at 25° C.±2° C./60% RH±5% RH maintained its physical stability for up to 6 months. Visible particulate matter was observed at 9 months, however, no visible particulate matter was observed at 12 months. The label claim remained essentially unchanged for up to 6 months. The total impurities remained at the level of 0.09%

TABLE 12

| | Citrate | | | | | | | | | | | |
|---|---|---|---|---|---|---|---|---|---|---|---|---|
| | Upright | | | | | | Inverted | | | | | |
| n = 2 | 0 | 1 M | 3 M | 6 M | 9 M | 12 M | 0 | 1 M | 3 M | 6 M | 9 M | 12 M |
| Label Claim (%) | 103.5 | 104.0 | NA | 103.9 | NA | 104.6 | 103.5 | 105.7 | 106.7 | 104.2 | 102.7 | 104.4 |
| Impurities (%)[1] | 0.09 | 0.09 | NA | 0.09 0.06 | NA | 0.09 0.09 | 0.09 | 0.09 | 0.09 | 0.09 0.06 | 0.09 0.08 | 0.09 0.09 |
| Total Impurities (%) | 0.09 | 0.09 | NA | 0.15 | NA | 0.18 | 0.09 | 0.09 | 0.09 | 0.15 | 0.17 | 0.18 |
| Appearance | Sample solution is transparent, no visible particulate matter | | NA | Sample solution is transparent, no visible particulate matter | NA | Clear solution, no visible particulate matter | Sample solution is transparent, no visible particulate matter | | | | Clear solution, no visible particulate matter | |
| pH | 4.5 | 4.7 | NA | 4.8 | NA | 4.6 | 4.5 | 4.7 | 4.7 | 4.8 | 4.8 | 4.6 |

The results demonstrate that the romidepsin formulation in citrate buffer at 25° C.±2° C./60% RH±5% RH RH maintained its physical stability for up to 6 months. No visible particulate matter was observed up to 12 months. The label claim remained essentially unchanged while the total impurities increased from 0.09% to 0.16% and 0.15% at 6 months and further to 0.18% at 12 months for upright and inverted storage condition, respectively (Table 12).

Table 13 demonstrates the test results for romidepsin liquid concentrate injection in acetate buffer stored at 25° C.±2° C./60% RH±5% RH up to 12 months.

after 6 months of storage at 25° C.±2° C./60% RH±5% RH, and increased to 0.16% and 0.15% at 12 months for upright and inverted storage conditions, respectively (Table 13).

Table 14 demonstrates the test results for romidepsin liquid concentrate injection in citrate buffer stored at 40° C.±2° C./75% RH±5% RH up to 6 months.

TABLE 13

| | Acetate | | | | | | | | | | | |
|---|---|---|---|---|---|---|---|---|---|---|---|---|
| | Upright | | | | | | Inverted | | | | | |
| n = 2 | 0 | 1 M | 3 M | 6 M | 9 M | 12 M | 0 | 1 M | 3 M | 6 M | 9 M | 12 M |
| Label Claim (%) | 105.2 | 107.8 | NA | 107.5 | NA | 106.9 | 105.2 | 107.8 | 109.6 | 107.6 | 106.6 | 107.8 |
| Impurities (%) | 0.09 | 0.09 | NA | 0.09 | NA | 0.09 0.07 | 0.09 | 0.09 | 0.09 | 0.09 | 0.09 0.05 | 0.09 0.06 |
| Total Impurities (%) | 0.09 | 0.09 | NA | 0.09 | NA | 0.16 | 0.09 | 0.09 | 0.09 | 0.09 | 0.14 | 0.15 |
| Appearance | Sample solution is transparent, no visible particulate matter | | NA | Sample solution is transparent, no visible particulate matter | [1] [2] | Clear solution, no visible particulate matter | Sample solution is transparent, no visible particulate matter | | | | Clear solution, no visible particulate matter | Clear solution, no visible particulate matter |
| pH | 4.0 | 4.2 | NA | 4.2 | NA | 4.1 | 4.0 | 4.2 | 4.1 | 4.2 | 4.1 | 4.2 |

[1]Sample solution is transparent. No visible particulate matter.
[2]Some visible particulate matter are observed.

TABLE 14

| n = 2 | Citrate | | | | | | | | | |
|---|---|---|---|---|---|---|---|---|---|---|
| | Upright | | | | | Inverted | | | | |
| | 0 | 2 W | 1 M | 3 M | 6 M | 0 | 2 W | 1 M | 3 M | 6 M |
| Label Claim (%) | 103.5 | 103.3 | 104.7 | 104.9 | 96.9 | 103.5 | 103.3 | 105.2 | 104.8 | 97.7 |
| Total Impurities (%) | 0.09 | 0.09 | 0.16 | 0.50 | 2.43 | 0.09 | 0.09 | 0.17 | 0.52 | 2.21 |
| Appearance | Sample solution is transparent, no visible particulate matter | | | | | Sample solution is transparent, no visible particulate matter | | | | |
| pH | 4.5 | 4.7 | 4.9 | 4.9 | 4.8 | 4.5 | 4.7 | 4.9 | 4.9 | 4.7 |

The results indicate that no visible particulate matter was observed for the romidepsin formulation in citrate buffer maintained at 40° C.±2° C./75% RH±5% RH for up to 6 month. However, the pH value increased from 4.5 to 4.7 at 2 weeks and further to 4.9 at 1 month. Label claim of the romidepsin formulation in citrate buffer remained essentially unchanged up to 3 months, but decreased from 103.5% at 0 time to 96.9% and 97.7% at 6 months for upright and inverted storage conditions, respectively. The total impurities remained 0.09% at 2 weeks, but increased to 0.16% and 0.17% at 1 month and further to 2.43% and 2.21% at 6 months for upright and inverted storage conditions, respectively (Table 14).

Table 15 demonstrates the test results for romidepsin liquid concentrate injection in acetate buffer stored at 40° C.±2° C./75% RH±5% RH up to 6 months.

TABLE 15

| n = 2 | Acetate | | | | | | | | | |
|---|---|---|---|---|---|---|---|---|---|---|
| | Upright | | | | | Inverted | | | | |
| | 0 | 2 W | 1 M | 3 M | 6 M | 0 | 2 W | 1 M | 3 M | 6 M |
| Label Claim (%) | 105.2 | 106.7 | 107.3 | 108.7 | 104.3 | 105.2 | 107.0 | 106.3 | 108.3 | 104.8 |
| Total Impurities (%) | 0.09 | 0.09 | 0.09 | 0.36 | 1.43 | 0.09 | 0.09 | 0.09 | 0.35 | 1.21 |
| Appearance | Sample solution is transparent, no visible particulate matter | | | Some visible particle matter | | Sample solution is transparent, no visible particulate matter | | | Some visible particle matter | |
| pH | 4.0 | 4.2 | 4.2 | 4.2 | 4.1 | 4.0 | 4.2 | 4.2 | 4.2 | 4.1 |

The results have shown that visible particulate matter was observed for the romidepsin formulation in acetate buffer at 3 months and 6 months stored at 40° C.±2° C./75% RH±5% RH. The pH value remained essentially unchanged. Label claim of the romidepsin formulation in acetate buffer remained essentially unchanged at 40° C.±2° C./75% RH±5% RH for up to 6 months. The total impurities remained at 0.09% level after 1 month of storage at 40° C.±2° C./75% RH±5% RH, but increased to 0.36% and 0.35% at 3 month and further to 1.43% and 1.21% at 6 months for upright and inverted storage conditions, respectively (Table 15).

Based on 12 months stability data, the romidepsin liquid concentrate formulation in acetate buffer is more stable than the romidepsin liquid concentrate formulation in citrate buffer due to lower total impurity content at accelerated storage condition.

All publications, patents, and patent applications mentioned in this specification are herein incorporated by reference to the same extent as if each individual publication, patent, or patent application was specifically and individually indicated to be incorporated by reference.

The present disclosure has been described above with reference to exemplary embodiments. However, those skilled in the art, having read this disclosure, will recognize that changes and modifications may be made to the exemplary embodiments without departing from the scope of the present disclosure. The changes or modifications are intended to be included within the scope of the present disclosure, as expressed in the following claims.

The invention claimed is:

1. A method of treating peripheral T-cell lymphoma (PTCL) or cutaneous T-cell lymphoma (CTCL) in a subject comprising administering to the subject a formulation comprising romidepsin in a concentration of 1 mg/mL to 10 mg/mL, propylene glycol (PG), ethanol (EtOH) and a citrate buffer, wherein said formulation is stable for at least 6 months at ambient temperature, and wherein the ratio of PG, EtOH and the citrate buffer in the formulation is 70% of PG, 20% of EtOH, and 10% of the citrate buffer, and wherein a pH of the formulation is in a range from 4.5 to 5.0.

2. The method of claim 1, wherein the formulation comprising romidepsin is a unit dosage form.

3. The method of claim 2, wherein the amount of romidepsin is between 2 and 20 mg per unit dosage form.

4. The method of claim 1, wherein the concentration of romidepsin is 5 mg/mL.

5. The method of claim 1, wherein romidepsin is administered intravenously.

6. The method of claim 5, wherein a dose of romidepsin is in a range of between 0.5 and 28 mg/m$^2$ body surface area is administered.

7. The method of claim 6, wherein the dose of romidepsin is in a range of between 8 and 14 mg/m$^2$ body surface area.

8. The method of claim 7 wherein the dose of romidepsin is about 8 mg/m² body surface area.

9. The method of claim 7, wherein the dose of romidepsin is about 10 mg/m² body surface area.

10. The method of claim 7, wherein the dose of romidepsin is about 12 mg/m² body surface area.

11. The method of claim 7, wherein the dose of romidepsin is about 14 mg/m² body surface area.

12. The method of claim 11, wherein the formulation is administered as an IV infusion over a 4 hour period on days 1, 8, and 15 of a 28 day cycle.

* * * * *